US007655669B2

(12) United States Patent
Manley et al.

(10) Patent No.: US 7,655,669 B2
(45) Date of Patent: Feb. 2, 2010

(54) PYRIMIDINEAMIDE DERIVATIVES AND THE USE THEREOF

(75) Inventors: Paul William Manley, Arlesheim (CH); Werner Breitenstein, Basel (CH); Sandra Jacob, Rantzwiller (FR); Pascal Furet, Thann (FR)

(73) Assignee: Novartis AG, Basel (CH)

( * ) Notice: Subject to any disclaimer, the term of this patent is extended or adjusted under 35 U.S.C. 154(b) by 332 days.

(21) Appl. No.: 10/528,913

(22) PCT Filed: Sep. 26, 2003

(86) PCT No.: PCT/EP03/10724

§ 371 (c)(1),
(2), (4) Date: Jan. 5, 2006

(87) PCT Pub. No.: WO2004/029038

PCT Pub. Date: Apr. 8, 2004

(65) Prior Publication Data
US 2006/0142577 A1 Jun. 29, 2006

(30) Foreign Application Priority Data
Sep. 27, 2002 (GB) .................. 0222514.2

(51) Int. Cl.
C07D 401/14 (2006.01)
A61K 31/506 (2006.01)
(52) U.S. Cl. ..................... 514/275; 544/324
(58) Field of Classification Search ............. 544/324; 514/275
See application file for complete search history.

(56) References Cited
U.S. PATENT DOCUMENTS 5,215,989 A 6/1993 Baldwin et al.
5,516,775 A 5/1996 Zimmermann et al.
5,521,184 A 5/1996 Zimmermann

FOREIGN PATENT DOCUMENTS

| EP | 0 233 461 | 8/1987 |
| EP | 0 564 409 | 10/1993 |
| EP | 0 588 762 | 3/1994 |
| GB | 2 369 359 | 5/2002 |
| WO | 0 564 409 A | 10/1993 |
| WO | WO 95/09847 | 4/1995 |
| WO | WO 95/09852 | 4/1995 |
| WO | WO 01/47507 | 7/2001 |
| WO | WO 01/64200 | 9/2001 |
| WO | 02 22597 A | 3/2002 |
| WO | WO 02/22597 | 3/2002 |
| WO | 02 93164 | 11/2002 |
| WO | WO 02/093164 | 11/2002 |

OTHER PUBLICATIONS

Traxler, Protein Tyrosine Kinase inhibitors in Cancer treatment, Expert Opinion on Therapeutic Patents, 7(6), pp. 571-588, 1997.*
Yano et al., Medline Abstract (Clinical Cancer Research, vol. 6, Issue 3, pp. 957-965), Mar. 2000.*
Cressey et al., Medline Abstract (BMC Cancer, vol. 5, p. 128) Oct. 2005.*
Simone, Onclogy: Introduction, Cecil Textbook of Medicine, 20$^{th}$ Edition, vol. 1, pp. 1004-1010, 1996.*
Buchdunger et al., "Selective Inhibition of the Platelet-Derived Growth Factor Signal Transduction Pathway by a Protein-Tyrosine Kinase Inhibitor of the 2-Phenylaminopyrimidine Class", *Proc Natl Acad Sci USA*, vol. 92, No. 7, pp. 2558-2562 (1995).
Buchdunger et al., "Inhibition of the Abl Protein-Tyrosine Kinase in Vitro and in Vivo by a 2-Phenylaminopyrimidine Derivative", *Cancer Res*, vol. 56, No. 1, pp. 100-104 (1996).
Carroll et al., "CGP 57148, A Tyrosine Kinase Inhibitor, Inhibits the Growth of Cells Expressing BCR-ABL, TEL-ABL, and TEL-PDGFR Fusion Proteins", *Blood*, vol. 90, No. 12, pp. 4947-4952 (1997).
Druker et al., "Effects of a Selective Inhibitor of the Abl Tyrosine Kinase on the Growth of Bcr-Abl Positive Cells", *Nat Med*, vol. 2, No. 5, pp. 561-566 (1996).
Druker et al., "Selective Killing of Bcr-Abl Positive Cells with a Specific Inhibitor of the Abl Tyrosine Kinase", Pezcoller Foundation Symposia, *Cancer Genes*, pp. 255-267 (1996).
Zimmermann et al., "Phenylamino-Pyrimidine (PAP) Derivatives: A New Class of Potent and Selective Inhibitors of Protein Kinase C (PKC)", *Arch Pharm Pharm Med Chem*, vol. 329, No. 7, pp. 371-376 (1996).
Zimmermann et al., "Phenylamino-Pyrimidine (PAP)—Derivatives: A New Class of Potent and Highly Selective PDGF-Receptor Autophosphorylation Inhibitors", *Bioorg Med Chem Lett*, vol. 6, No. 11, pp. 1221-1226 (1996).
Zimmermann et al., "Potent and Selective Inhibitors of the Abl-Kinase: Phenylamino-Pyrimidine (PAP) Derivatives", *Bioorg Med Chem Lett*, vol. 7, No. 2, pp. 187-192 (1997).

* cited by examiner

*Primary Examiner*—Deepak Rao

(57) ABSTRACT

The invention relates to novel substituted N-(3-benzoylaminophenyl)-4-pyridyl-2-pyrimidinamine derivatives, processes for the preparation thereof, pharmaceutical compositions containing same, the use thereof optionally in combination with one or more other pharmaceutically active compounds for the therapy of a disease which responds to an inhibition of protein kinase activity, especially a neoplastic disease, and a method for the treatment of such a disease.

9 Claims, No Drawings

PYRIMIDINEAMIDE DERIVATIVES AND THE USE THEREOF

This application is a 371 of PCT/EP03/10724 filed Sep. 26, 2003.

The invention relates to novel substituted N-(3-benzoylaminophenyl)-4-pyridyl-2-pyrimidinamine derivatives, processes for the preparation thereof, pharmaceutical compositions containing same, the use thereof optionally in combination with one or more other pharmaceutically active compounds for the therapy of a disease which responds to an inhibition of protein kinase activity, especially a neoplastic disease, and a method for the treatment of such a disease.

Protein kinases (PKs) are enzymes which catalyze the phosphorylation of specific serine, threonine or tyrosine residues in cellular proteins. These post-translational modifications of substrate proteins act as molecular switches regulating cell proliferation, activation and/or differentiation. Aberrant or excessive PK activity has been observed in many disease states including benign and malignant proliferative disorders. In a number of cases, it has been possible to treat diseases, such as proliferative disorders, by making use of PK inhibitors in vitro and in vivo.

In view of the large number of protein kinase inhibitors and the multitude of proliferative and other PK-related diseases, there is an ever-existing need to provide novel classes of compounds that are useful as PK inhibitors and thus in the treatment of these PK related diseases. What is required are new classes of pharmaceutically advantageous PK inhibiting compounds.

The Philadelphia Chromosome is a hallmark for chronic myelogenous leukemia (CML) and carries a hybrid gene that contains N-terminal exons of the bcr gene and the major C-terminal part (exons 2-11) of the c-abl gene. The gene encodes either a 190 kD, 210 kD, or 230 kD chimeric protein, depending on which of three alternative break points in bcr is involved. The Abl-part of the Bcr-Abl protein contains the Abl-tyrosine kinase which is tightly regulated in the wild type c-Abl, but constitutively activated in the Bcr-Abl fusion protein. This deregulated tyrosine kinase interacts with multiple cellular signaling pathways leading to transformation and deregulated proliferation of the cells (Lugo et al., Science 247 1079 [1990]).

The p210 Bcr-Abl is expressed in 95% of CML patients and in approximately 33% of patients with acute lymphoblastic leukemia (ALL). Expression of the smaller p190 kD protein occurs more frequently in ALL, but rarely in CML and is characterized clinically by prominent monocytosis. The 230 kD fusion protein is associated with the rare chronic neutrophilic leukemia, whose progression to blast crisis is slow. In advanced stage CML and in ALL in particular, clones frequently emerge in which the kinase domain of the Bcr-Abl protein is mutated. Such mutants include for example the E225V and M351 T transformations (Shah et al., Cancer Research 2, 117-225 [2002]).

Mutant ras oncogenes are frequently associated with tumor progression. The Ras proteins are expressed from three different genes, namely, Neuroblastoma (N)-ras, Harvey (Ha)-ras and Kirsten (K)-ras. K-ras mutated most often in solid tumors, such as colon, lung and especially pancreatic cancer, and N-ras in haematopoietic tumors, predominantly acute myelogenous leukemia (Lyons et al., Endocrine-Related Cancer 8, 219 [2001]). Ras has been shown to regulate several pathways that contribute to cellular transformation, including e.g. the Raf/MEK pathway by binding to and activating Raf kinase.

The N-(3-benzoylaminophenyl)-4-pyridyl-2-pyrimidinamine derivatives of formula 1, described below in more detail, show excellent inhibition of protein kinase activity, especially inhibition of one or more tyrosine kinases, such Bcr-Abl, mutant Bcr-Abl, c-Abl, Raf, the receptor tyrosine kinases PDGF-R, Flt3, VEGF-R, EGF-R, and c-Kit, as well as combinations of two or more of these. In particular, the compounds of the invention show high potency against some of the mutant forms of Bcr-Abl, which have been observed in drug-resistant patients. In view of these activities, the compounds can be used for the treatment of diseases related to especially aberrant or excessive activity of such types of kinases, e.g. for the treatment of particular cases of leukemia and of solid tumors such as colon, lung and pancreatic cancer.

The invention relates to a compound of formula 1,

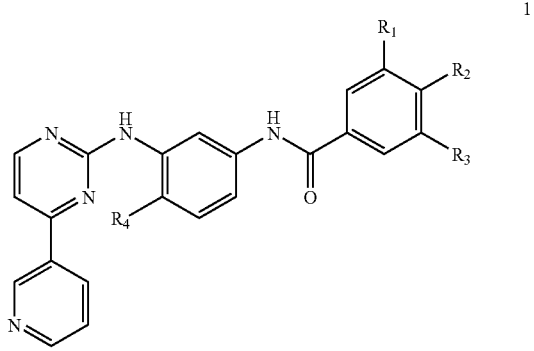

wherein
$R_1$ represents hydrogen and $R_2$ represents $NR_5R_6$, or $R_1$ represents $NR_5R_6$ and $R_2$ represents hydrogen;
$R_3$ represents lower alkyl, fluoroalkyl, hydroxyalkyl or carbamoyl;
$R_4$ represents hydrogen, lower alkyl or halogen; and
$R_5$ and $R_6$ represent, independently of each other, hydrogen, lower alkyl, hydroxy-lower alkyl, lower alkoxy-lower alkyl, lower acyloxy-lower alkyl, carboxy-lower alkyl, lower alkoxycarbonyl-lower alkyl, amino-lower alkyl, lower alkylamino-lower alkyl, di(lower alkyl)amino-lower alkyl, N-lower alkylpiperidinyl, N-lower alkylpyrrolidinyl, or lower acyl, or $R_5R_6$ together represent alkylene with four, five or six carbon atoms, oxa-lower alkylene with one oxygen and three or four carbon atoms, or aza-lower alkylene with one nitrogen and three or four carbon atoms wherein the nitrogen atom is unsubstituted or substituted by lower alkyl, hydroxy-lower alkyl or lower alkoxy-lower alkyl, and wherein lower alkylene in each case may be partially or totally unsaturated and/or the carbon atoms of lower alkylene may be substituted by lower alkyl, hydroxy or lower alkoxy;

and a N-oxide or a pharmaceutically acceptable salt of such a compound.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomerpure diastereomers.

The invention relates also to possible tautomers of the compounds of formula 1.

Lower alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or methyl. Preferably lower alkyl is methyl, propyl or tert-butyl.

Lower acyl is preferably formyl or lower alkylcarbonyl, in particular acetyl.

Hydroxyalkyl is especially hydroxy-lower alkyl, preferably hydroxymethyl, 2-hydroxyethyl or 2-hydroxy-2-propyl.

Fluoroalkyl is especially fluoro-lower alkyl, preferably trifluoromethyl or pentafluoroethyl.

Halogen is especially fluorine, chlorine, bromine, or iodine, especially fluorine, chlorine, or bromine.

Lower alkoxy is especially methoxy, ethoxy, isopropyloxy, or tert-butyloxy.

Lower alkoxycarbonyl is especially tert-butoxycarbonyl, iso-propoxycarbonyl, methoxycarbonyl or ethoxycarbonyl.

Salts are especially the pharmaceutically acceptable salts of compounds of formula 1.

Such salts are formed, for example, as acid addition salts, preferably with organic or inorganic acids, from compounds of formula 1 with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compounds of formula 1 and N-oxides thereof have valuable pharmacological properties, as described hereinbefore and hereinafter.

The efficacy of the compounds of the invention as inhibitors of c-Abl, Bcr-Abl, Raf and VEGF-receptor tyrosine kinase activity can be demonstrated as follows:

Test for activity against c-Abl protein tyrosine kinase. The test is conducted as a filter binding assay as follows: The His-tagged kinase domain of c-Abl is cloned and expressed in the baculovirus/Sf9 system as described by Bhat et al., J. Biol. Chem. 272, 16170-5 (1997). A protein of 37 kD (c-Abl kinase) is purified by a two-step procedure over a cobalt metal chelate column followed by an anion exchange column with a yield of 1-2 mg/L of Sf9 cells. The purity of the c-Abl kinase is >90% as judged by SDS-PAGE after Coomassie blue staining. The assay contains: c-Abl kinase (50 ng), 20 mM Tris-HCl, pH 7.5, 10 mM $MgCl_2$, 10 μM $Na_3VO_4$, 1 mM DTT and 0.06 μCi/assay $[\gamma^{33}P]$-ATP (5 μM ATP) using 30 μg/mL poly-Ala,Glu,Lys,Tyr-6:2:5:1 (Poly-AEKY, Sigma P1152) in the presence of 1% DMSO, total volume of 30 μL. Reactions are terminated by adding 10 μL of 250 mM EDTA, and 30 μL of the reaction mixture is transferred onto Immobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 μL 0.5% $H_3PO_4$. Membranes are removed and washed on a shaker with 0.5% $H_3PO_4$ (4 times) and once with ethanol. Membranes are counted after drying at ambient temperature, mounting in Packard TopCount 96-well frame, and addition of 10 μL/well of Microscint™ (Packard).

Test for activity against Bcr-Abl. The murine myeloid progenitor cell line 32Dcl3 transfected with the p210 Bcr-Abl expression vector pGDp210Bcr/Abl (32D-bcr/abl) was obtained from J. Griffin (Dana Faber Cancer Institute, Boston, Mass., USA). The cells express the fusion Bcr-Abl protein with a constitutively active Abl kinase and proliferate growth factor independent. The cells are expanded in RPMI 1640 (AMIMED), 10% fetal calf serum, 2 mM glutamine (Gibco) ("complete medium"), and a working stock is prepared by freezing aliquots of $2\times10^6$ cells per vial in freezing medium (95% FCS, 5% DMSO (SIGMA)). After thawing, the cells are used during maximally 10-12 passages for the experiments.

For cellular assays, compounds are dissolved in DMSO and diluted with complete medium to yield a starting concentration of 10 μM followed by preparation of serial 3-fold dilutions in complete medium. 200,000 32D-Bcr/Abl cells in 50 μL complete medium are seeded per well in 96 well round bottom tissue culture plates. 50 μL per well of serial 3-fold dilutions of the test compound are added to the cells in triplicates. Untreated cells are used as control. The compound is incubated together with the cells for 90 min at 37° C., 5% $CO_2$, followed by centrifugation of the tissue culture plates at 1300 rpm (Beckman GPR centrifuge) and removal of the supernatants by careful aspiration taking care not to remove any of the pelleted cells. The cell pellets are lysed by addition of 150 μL lysis buffer (50 mM Tris/HCl, pH 7.4, 150 mM sodium chloride, 5 mM EDTA, 1 mM EGTA, 1% NP-40, 2 mM sodium ortho-vanadate, 1 mM PMSF, 50 μg/mL aprotinin and 80 μg/mL leupeptin) and either used immediately for the ELISA or stored frozen in the plates at −20° C. until usage.

Black ELISA plates (Packard HTRF-96 black plates) are precoated over night at 4° C. with 50 ng/well of the rabbit polyclonal anti-abl-SH3 domain Ab 06-466 from Upstate in 50 μL PBS. After washing 3 times with 200 μL/well PBS containing 0.05% Tween20 (PBST) and 0.5% TopBlock (Juro), residual protein binding sites are blocked with 200 μL/well PBST, 3% TopBlock for 4 h at room temperature followed by incubation with 50 μL lysates of untreated or compound-treated cells (20 μg total protein per well) for 3-4 h at 4° C. After 3 washings, 50 μL/well anti-phosphotyrosine Ab PY20(AP) labeled with alkaline phosphatase (Zymed) diluted to 0.2 μg/mL in blocking buffer is added and incubated over night (4° C.). For all incubation steps the plates are covered with plate sealers (Costar). Finally, the plates are washed another three times with washing buffer and once with deionized water before addition of 90 μL/well of the AP-substrate CDPStar RTU with Emerald II. The plates, now sealed with Packard TopSeal™-A plate sealers, are incubated for 45 min at room temperature in the dark and luminescence is quantified by measuring counts per second (CPS) with a Packard Top Count Microplate Scintillation Counter (Top Count).

The difference between the ELISA-readout (CPS) obtained for with the lysates of the untreated 32D-Bcr/Abl cells and the readout for the assay-background (all components, but without cell lysate) is calculated and taken as 100% reflecting the constitutively phosphorylated Bcr-Abl protein present in these cells. The activity of the compound on the Bcr-Abl kinase activity is expressed as percent reduction of the Bcr-Abl phosphorylation. The values for the $IC_{50}$ and $IC_{90}$ are determined from the dose response curves by graphical extrapolation.

Test for activity against mutant Bcr-Abl: The activity of compounds on the M351T mutant Bcr-Abl kinase activity is assessed as described above, except that 32Dcl3 cells transfected with mutant Bcr-Abl in place of p210 Bcr-Abl are utilised.

c-Raf-1 protein kinase assay: Recombinant c-Raf-1 protein is obtained by triple infection of Sf21 cells with GST-c-Raf-1 recombinant baculovirus together with v-Src and v-Ras recombinant baculoviruses that are required for active c-Raf-1 kinase production (Williams et al., PNAS 1992; 89:2922-6). Active Ras (v-Ras) is required to recruit c-Raf-1 to the cell membrane and v-Src to phosphorylate c-Raf-1 to fully activate it. Cells are seeded at $2.5 \times 10^7$ cells per 150 mm dish and allowed to attach to a 150 mm dish for 1 hr at RT. Media (SF900II containing 10% FBS) is aspirated and recombinant baculovirus GST-c-Raf-1, v-Ras and v-Src are added at MOI of 3.0, 2.5 and 2.5, respectively, in a total volume of 4-5 mL. Cells are incubated for 1 hr at RT and then 15 mL of medium is added. Infected cells are incubated for 48-72 hr at 27° C. Infected Sf21 cells are scraped and collected into a 50 mL tube and centrifuged for 10 min at 4° C. at 1100 g in a Sorvall centrifuge. The cell pellet is washed once with ice cold PBS and lysed with 0.6 mL lysis buffer per $2.5 \times 10^7$ cells. Complete lysis of cells is achieved after 10 min on ice with occasional pipetting. The cell lysates are centrifuged for 10 min at 4° C. at 14,500 g in a Sorvall centrifuge with SS-34 rotor and the supernatant is transferred to a fresh tube and stored at −80° C. c-Raf-1 is purified from cell lysates using 100 μL of packed glutathione-sepharose 4B beads equilibrated in ice cold PBS per $2.5 \times 10^7$ cells. GST-c-Raf-1 is allowed to bind to the beads at 4° C. for 1 hr with rocking. Bound GST-c-Raf-1 with beads is transferred to a column. The column is washed once with lysis buffer and twice with ice cold Tris buffered saline. Ice cold elution buffer is added and column flow is stopped to allow the free glutathione to disrupt the interaction of GST-c-Raf-1 with glutathione sepharose beads. Fractions (1 mL) are collected into pre-chilled tubes. Each tube contains 10% glycerol (final concentration) to maintain kinase activity during freeze thaw cycles. Purified fractions of GST-c-Raf-1 kinase protein are stored at −80° C.

IκB is used as substrate for the c-Raf-1 kinase. IκB is expressed in bacteria as a His-tagged protein BL21. LysS bacteria containing the IκB plasmid are grown to an OD600 of 0.6 in LB medium, then induced to express the IκB with IPTG (final concentration of 1 mM) for 3 hrs at 37° C. and then bacteria are lysed by sonication (microtip limit setting for 3 times at 1 min each in sonication buffer [50 mM Tris pH 8.0, 1 mM DTT, 1 mM EDTA] and centrifuged at 10,000 g for 15 min. The supernatant is mixed with ammonium sulfate to give a final concentration of 30%. This mixture is rocked for 15 min at 4 C then spun at 10,000 g for 15 min. The pellet is resuspended in binding buffer (Novagen) containing 10 mM BSA. This solution is applied to Ni-agarose (Novagen) and washed according to the Novagen manual. IκB is eluted from the column using elution buffer (0.4 M imidazole, 0.2 M NaCl, 8 mM Tris pH 7.9). Fractions containing protein are dialysed in 50 mM Tris pH 8, 1 mM DTT.

The activity of c-Raf-1 protein kinase is assayed in the presence or absence of inhibitors, by measuring the incorporation of $^{33}P$ from [$\gamma^{33}P$] ATP into IκB. The assay is carried out in 96-well plates at ambient temperature for 60 min. It contains (total volume of 30 μL): c-Raf-1 kinase (400 ng), 25 mM Tris.HCl, pH 7.5, 5 mM $MgCl_2$, 5 mM $MnCl_2$, 10 μM $Na_3VO_4$, 1 mM DTT and 0.3 μCi/assay [$\gamma^{33}P$]-ATP (10 μM ATP) using 600 ng IκB in the presence of 1% DMSO. Reactions are terminated by adding 10 μL of 250 mM EDTA and 30 μL of the reaction mixture is transferred onto Immobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 μL 0.5% $H_3PO_4$. Membranes are removed and washed 4× on a shaker with 0.5% $H_3PO_4$, once with ethanol. Membranes are counted after drying at ambient temperature, mounting in Packard TopCount 96-well frame, and addition of 10 μL/well of Microscint™ (Packard).

Test for activity against VEGF-receptor tyrosine kinase. The test is conducted using Flt-1 VEGF-receptor tyrosine kinase. The detailed procedure is as follows: 30 μL kinase solution (10 ng of the kinase domain of Flt-1, Shibuya et al., Oncogene 5, 519-24 [1990]) in 20 mM Tris.HCl pH 7.5, 3 mM manganese dichloride ($MnCl_2$), 3 mM magnesium chloride ($MgCl_2$), 10 μM sodium vanadate, 0.25 mg/mL polyethyleneglycol (PEG) 20000, 1 mM dithiothreitol and 3 μg/μL poly(Glu,Tyr) 4:1 (Sigma, Buchs, Switzerland), 8 μM [$^{33}P$]-ATP (0.2 μCi), 1% DMSO, and 0 to 100 μM of the compound to be tested are incubated together for 10 minutes at room temperature. The reaction is then terminated by the addition of 10 μL 0.25 M ethylenediaminetetraacetate (EDTA) pH 7. Using a multichannel dispenser (LAB SYSTEMS, USA), an aliquot of 20 μL is applied to a PVDF (=polyvinyl difluoride) Immobilon P membrane (Millipore, Bedford, USA), through a Gibco-BRL microtiter filter manifold and connected to a vacuum. Following complete elimination of the liquid, the membrane is washed 4 times successively in a bath containing 0.5% phosphoric acid ($H_3PO_4$) and once with ethanol, incubated for 10 minutes each time while shaking, then mounted in a Hewlett Packard TopCount Manifold and the radioactivity measured after the addition of 10 μL Microscint® (β-scintillation counter liquid). $IC_{50}$-values are determined by linear regression analysis of the percentages for the inhibition of each compound in at least four concentrations (as a rule 0.01, 0.1, 1.0 and 10 μmol). The $IC_{50}$-values that can be found with compounds of formula 1 are in the range of 1 to 10,000 nM, preferably in the range of 1 to 100 nM.

The inhibition of VEGF-induced KDR-receptor autophosphorylation can be confirmed with a further in vitro experiment in cells: transfected CHO cells, which permanently express human VEGF receptor (KDR), are seeded in complete culture medium with 10% fetal calf serum (FCS) in swell cell-culture plates and incubated at 37° C. under 5% $CO_2$ until they show about 80% confluency. The compounds to be tested are then diluted in culture medium (without FCS, with 0.1% bovine serum albumin) and added to the cells. (Controls comprise medium without test compounds). After two hours of incubation at 37° C., recombinant VEGF is added; the final VEGF concentration is 20 ng/mL). After a further five minute incubation at 37° C., the cells are washed twice with ice-cold PBS (phosphate-buffered saline) and immediately lysed in 100 μL lysis buffer per well. The lysates are then centrifuged to remove the cell nuclei, and the protein concentrations of the supernatants are determined using a commercial protein assay (BIORAD). The lysates can then either be immediately used or, if necessary, stored at −20° C.

A sandwich ELISA is carried out to measure the KDR-receptor phosphorylation: a monoclonal antibody to KDR (for example Mab 1495.12.14) is immobilized on black ELISA plates (OptiPlate™ HTRF-96 from Packard). The plates are then washed and the remaining free protein-binding sites are saturated with 1% BSA in PBS. The cell lysates (20 μg protein per well) are then incubated in these plates overnight at 4° C. together with an anti-phosphotyrosine antibody coupled with alkaline phosphatase (PY20:AP from Transduction Laboratories). The plates are washed again and the binding of the antiphosphotyrosine antibody to the captured phosphorylated receptor is then demonstrated using a luminescent AP substrate (CDP-Star, ready to use, with Emerald II; TROPIX). The luminescence is measured in a Packard Top Count Microplate Scintillation Counter (Top Count). The difference between the signal of the positive control (stimulated with VEGF) and that of the negative control (not stimulated with VEGF) corresponds to VEGF-induced KDR-receptor phosphorylation (=100%). The activity of the tested substances is calculated as % inhibition of VEGF-induced KDR-receptor phosphorylation, wherein the concentration of substance that induces half the maximum inhibition is defined as the ED50 (effective dose for 50% inhibition). Compounds of formula 1 here preferably show ED50 values in the range of 0.25 nM to 1000 nM, preferably 0.25 to 250 nM.

A compound of formula 1 or a N-oxide thereof inhibits to varying degrees also other tyrosine kinases involved in signal transduction which are mediated by trophic factors, for example Raf, Bcr-Abl and Abl kinase, Arg, kinases from the Src family, especially c-Src kinase, Lck, and Fyn; also kinases of the EGF family, for example, c-erbB2 kinase (HER-2), c-erbB3 kinase, c-erbB4 kinase; insulin-like growth factor receptor kinase (IGF-1 kinase), especially members of the PDGF-receptor tyrosine kinase family, such as PDGF-receptor kinase, CSF-1-receptor kinase, Kit-receptor kinase and VEGF-receptor kinase; and also serine/threonine kinases, all of which play a role in growth regulation and transformation in mammalian cells, including human cells.

The inhibition of c-erbB2 tyrosine kinase (HER-2) can be measured, for example, in the same way as the inhibition of EGF-R protein kinase, using known procedures.

On the basis of these studies, a compound of formula 1 according to the invention shows therapeutic efficacy especially against disorders dependent on protein kinase, especially proliferative diseases.

On the basis of their efficacy as inhibitors of VEGF-receptor tyrosine kinase activity, the compounds of the formula 1 primarily inhibit the growth of blood vessels and are thus, for example, effective against a number of diseases associated with deregulated angiogenesis, especially diseases caused by ocular neovascularisation, especially retinopathies, such as diabetic retinopathy or age-related macula degeneration, psoriasis, haemangioblastoma, such as haemangioma, mesangial cell proliferative disorders, such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, diabetes, endometriosis, chronic asthma, and especially neoplastic diseases (solid tumors, but also leukemias and other "liquid tumors", especially those expressing c-kit, KDR, Flt-1 or Flt-3), such as especially breast cancer, cancer of the colon, lung cancer (especially small-cell lung cancer), cancer of the prostate or Kaposi's sarcoma. A compound of formula 1 (or an N-oxide thereof) inhibits the growth of tumours and is especially suited to preventing the metastatic spread of tumors and the growth of micrometastases.

A compound of formula 1 can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of formula 1 can besides or in addition be administered especially for tumor therapy, such as leukemia therapy, in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Therapeutic agents for possible combination are especially one or more antiproliferative, cytostatic or cytotoxic compounds, for example a chemotherapeutic agent or several agents selected from the group which includes, but is not limited to, an inhibitor of polyamine biosynthesis, an inhibitor of a protein kinase, especially of a serine/threonine protein kinase, such as protein kinase C, or of a tyrosine protein kinase, such as the EGF receptor tyrosine kinase, e.g. PKI166, the VEGF receptor tyrosine kinase, e.g. PTK787, or the PDGF receptor tyrosine kinase, e.g. ST1571, a cytokine, a negative growth regulator, such as TGF-β or IFN-β, an aromatase inhibitor, e.g. letrozole or anastrozole, an inhibitor of the interaction of an SH2 domain with a phosphorylated protein, antiestrogens, topoisomerase I inhibitors, such as irinotecan, topoisomerase 11 inhibitors, microtubule active agents, e.g. paclitaxel, discodermolide or an epothilone, alkylating agents, antineoplastic antimetabolites, such as gemcitabine or capecitabine, platin compounds, such as carboplatin or cisplatin, anti-angiogenic compounds, gonadorelin agonists, anti-androgens, bisphosphonates, e.g. AREDIA® or ZOMETA®, and trastuzumab. Preferred therapeutic agents for combination are especially selected from the group comprising indarubicin, cytarabine, interferon, hydroxyurea and bisulfan. The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

A compound according to the invention is not only for the (prophylactic and preferably therapeutic) management of humans, but also for the treatment of other warm-blooded animals, for example of commercially useful animals, for example rodents, such as mice, rabbits or rats, or guinea-pigs. Such a compound may also be used as a reference standard in the test systems described above to permit a comparison with other compounds.

In general, the invention relates also to the use of a compound of formula 1 or a N-oxide thereof for the inhibition of tyrosine kinase activity, either in vitro or in vivo.

With the groups of preferred compounds of formula 1 and N-oxides thereof mentioned hereinafter, definitions of substituents from the general definitions mentioned hereinbefore may reasonably be used, for example, to replace more general definitions with more specific definitions or especially with definitions characterized as being preferred.

In particular, the invention relates to compounds of formula 1, wherein $R_1$ represents hydrogen and $R_2$ represents $NR_5R_6$, or $R_1$ represents $NR_5R_6$ and $R_2$ represents hydrogen;

$R_3$ represents lower alkyl, fluoroalkyl, hydroxyalkyl or carbamoyl;

$R_4$ represents lower alkyl; and $R_5$ and $R_6$ represent, independently of each other, hydrogen, lower alkyl, hydroxy-lower alkyl, lower alkoxy-lower alkyl, lower acyloxy-lower alkyl, carboxy-lower alkyl, lower alkoxycarbonyl-lower alkyl, amino-lower alkyl, lower alkylamino-lower alkyl, di(lower alkyl)amino-lower alkyl, N-lower alkylpiperidinyl, N-lower alkylpyrrolidinyl, or lower acyl, or $R_5R_6$ together represent alkylene with four, five or six carbon atoms, oxa-lower alkylene with one oxygen and three or four carbon atoms, or aza-lower alkylene with one nitrogen and three or four carbon atoms wherein the nitrogen atom is unsubstituted or substituted by lower alkyl, hydroxy-lower alkyl or lower alkoxy-lower alkyl, and wherein lower alkylene in each case may be partially or totally unsaturated and/or the carbon atoms of lower alkylene may be substituted by lower alkyl, hydroxy or lower alkoxy;

and a N-oxide or a pharmaceutically acceptable salt of such a compound.

More particular, the invention relates to compounds of formula 1, wherein $R_1$ represents hydrogen and $R_2$ represents $NR_5R_6$, or $R_1$ represents $NR_5R_6$ and $R_2$ represents hydrogen;

$R_3$ represents trifluoromethyl;

$R_4$ represents methyl; and $R_5$ and $R_6$ represent, independently of each other, hydrogen, lower alkyl, hydroxy-lower alkyl, lower alkoxy-lower alkyl, lower acyloxy-lower alkyl, carboxy-lower alkyl, lower alkoxycarbonyl-lower alkyl, amino-lower alkyl, lower alkylamino-lower alkyl, di(lower alkyl)amino-lower alkyl, N-lower alkylpiperidinyl, N-lower alkylpyrrolidinyl, or acetyl, or $R_5R_6$ together represent alkylene with four, five or six carbon atoms, oxa-lower alkylene with one oxygen and three or four carbon atoms, or aza-lower alkylene with one nitrogen and three or four carbon atoms wherein the nitrogen atom is unsubstituted or substituted by lower alkyl, hydroxy-lower alkyl or lower alkoxy-lower alkyl, and wherein lower alkylene in each case may be partially or totally unsaturated and/or the carbon atoms of lower alkylene may be substituted by lower alkyl, hydroxy or lower alkoxy;

and a N-oxide or a pharmaceutically acceptable salt of such a compound.

More particular, the invention relates to compounds of formula 1, wherein $R_1$ represents hydrogen and $R_2$ represents $NR_5R_6$, or $R_1$ represents $NR_5R_6$ and $R_2$ represents hydrogen;

$R_3$ represents trifluoromethyl;

$R_4$ represents methyl; and $R_5$ and $R_6$ represent, independently of each other, hydrogen, lower alkyl, hydroxy-lower alkyl, amino-lower alkyl, lower alkylamino-lower alkyl, di(lower alkyl)amino-lower alkyl, N-lower alkylpiperidinyl, or lower acyl, or $R_5R_6$ together represent alkylene with four or five carbon atoms, oxa-lower alkylene with one oxygen and three or four carbon atoms, or aza-lower alkylene with one nitrogen and three or four carbon atoms wherein the nitrogen atom is unsubstituted or substituted by lower alkyl, hydroxy-lower alkyl or lower alkoxy-lower alkyl, and wherein lower alkylene in each case may be partially or totally unsaturated and/or the carbon atoms of lower alkylene may be substituted by lower alkyl;

and a N-oxide or a pharmaceutically acceptable salt of such a compound.

Preferred are compounds of formula 1, wherein $R_1$ represents hydrogen and $R_2$ represents $NR_5R_6$, or $R_1$ represents $NR_5R_6$ and $R_2$ represents hydrogen;

$R_3$ represents trifluoromethyl;

$R_4$ represents methyl; and $R_5$ and $R_6$ represent, independently of each other, hydrogen, lower alkyl, di(lower alkyl)amino-lower alkyl, N-lower alkylpiperidinyl, or lower acetyl, or $R_5R_6$ together represent alkylene with four or five carbon atoms, oxa-lower alkylene with one oxygen and four carbon atoms, or aza-lower alkylene with one nitrogen and three or four carbon atoms wherein the nitrogen atom is unsubstituted or substituted by lower alkyl, and wherein aza-lower alkylene may be unsaturated and/or the carbon atoms of aza-lower alkylene may be substituted by lower alkyl;

and a N-oxide or a pharmaceutically acceptable salt of such a compound.

Especially preferred are compounds of formula 1, wherein $R_1$ represents hydrogen and $R_2$ represents $NR_5R_6$, or $R_1$ represents $NR_5R_6$ and $R_2$ represents hydrogen;

$R_3$ represents trifluoromethyl;

$R_4$ represents methyl; and $R_5$ and $R_6$ represent, independently of each other, hydrogen, methyl, ethyl, 2-dimethylaminoethyl, 4-methyl-1-piperidinyl, or acetyl, or $NR_5R_6$ together represent pyrrolidino, piperidino, morpholino, N-methylpiperazino, 1H-imidazolyl, 1H-2-methylimidazolyl, 1H-4-methylimidazolyl or 1H-2,4-dimethylimidazolyl;

and a N-oxide or a pharmaceutically acceptable salt of such a compound.

Particularly preferred are the compounds of the Examples.

Especially, the invention relates to the use of a compound of formula 1 or of a N-oxide or a possible tautomer thereof or of a pharmaceutically acceptable salt of such a compound for the preparation of a pharmaceutical composition for the treatment of a disease which responds to an inhibition of protein kinase activity, wherein the disease is a neoplastic disease.

More particularly, the invention relates to the use of a compound of the formula 1 or of a N-oxide or a possible tautomer thereof; or of a pharmaceutically acceptable salt of such a compound for the preparation of a pharmaceutical composition for the treatment of leukemia which responds to an inhibition of the Raf and/or Abl tyrosine kinase activity.

Furthermore, the invention relates to the use of a compound of formula 1 or of a N-oxide or a possible tautomer thereof or of a pharmaceutically acceptable salt of such a compound in the treatment of a disease, which responds to an inhibition of protein kinase activity.

Furthermore, the invention provides a method for the treatment of a disease which responds to an inhibition of protein kinase activity, which comprises administering a compound of formula 1 or a N-oxide or a pharmaceutically acceptable salt thereof, wherein the radicals and symbols have the meanings as defined above, in a quantity effective against said disease, to a warm-blooded animal requiring such treatment.

A compound of the invention may be prepared by processes that, though not applied hitherto for the new compounds of the present invention, are known per se, especially a process characterized in that for the synthesis of a compound of the formula 1 wherein the symbols $R_1$, $R_2$, $R_3$ and $R_4$ are as defined for a compound of the formula 1, a substituted benzoic acid of formula 2

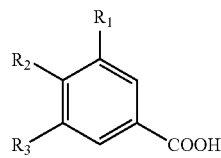

2 wherein $R_1$, $R_2$ and $R_3$ are as defined for a compound of formula 1, or a derivative thereof wherein the carboxy group —COOH is in activated form, is reacted with a 3-(4-(3-pyridyl)-2-pyrimidinamino)aniline of the formula 3

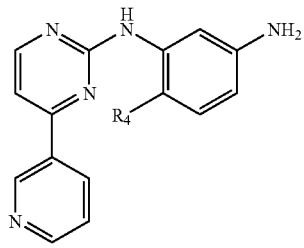

3 wherein $R_4$ is as defined for a compound of the formula 1, optionally in the presence of a dehydrating agent and an inert base and/or a suitable catalyst, and optionally in the presence of an inert solvent;

where the above starting compounds of formula 2 and 3 may also be present with functional groups in protected form if necessary and/or in the form of salts, provided a salt-forming group is present and the reaction in salt form is possible;

any protecting groups in a protected derivative of a compound of the formula 1 are removed;

and, if so desired, an obtainable compound of formula 1 is converted into another compound of formula 1 or a N-oxide thereof, a free compound of formula 1 is converted into a salt, an obtainable salt of a compound of formula 1 is converted into the free compound or another salt, and/or a mixture of isomeric compounds of formula 1 is separated into the individual isomers.

A derivative of the compound of formula 2 wherein the carboxy group is in activated form is especially a reactive ester, a reactive anhydride or a reactive cyclic amide.

Reactive esters of the acid of formula 2 are especially esters unsaturated at the linking carbon atom of the esterifying radical, for example esters of the vinyl ester type, such as actual vinyl esters (obtainable, for example, by transesterification of a corresponding ester with vinyl acetate; activated vinyl ester method), carbamoylvinyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N,N'-dicyclohexylcarbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters suitably substituted by electron-attracting substituents (obtainable, for example, by treatment of the corresponding acid with a suitably substituted phenol, for example 4-nitrophenol, 4-methylsulfonyl-phenol, 2,4,5-trichlorophenol, 2,3,4,5,6-pentachloro-phenol or 4-phenyldiazophenol, in the presence of a condensation agent, such as N,N'-dicyclohexyl-carbodiimide; activated aryl esters method), cyanomethyl esters (obtainable, for example, by treatment of the corresponding acid with chloroacetonitrile in the presence of a base; cyanomethyl esters method), thio esters, especially unsubstituted or substituted, for example nitro-substituted, phenylthio esters (obtainable, for example, by treatment of the corresponding acid with unsubstituted or substituted, for example nitro-substituted, thiophenols, inter alia by the anhydride or carbodiimide method; activated thiol esters method), amino or amido esters (obtainable, for example, by treatment of the corresponding acid with an N-hydroxy-amino or N-hydroxy-amido compound, for example N-hydroxy-succinimide, N-hydroxy-piperidine, N-hydroxy-phthalimide or 1-hydroxy-benzotriazole, for example by the anhydride or carbodiimide method; activated N-hydroxy esters method), or silyl esters (which are obtainable, for example, by treatment of the corresponding acid with a silylating agent, for example hexamethyl disilazane, and react readily with hydroxy groups but not with amino groups).

Anhydrides of the acid of formula 2 may be symmetric or preferably mixed anhydrides of that acid, for example anhydrides with inorganic acids, such as acid halides, especially acid chlorides (obtainable, for example, by treatment of the corresponding acid with thionyl chloride, phosphorus pentachloride or oxalyl chloride; acid chloride method), azides (obtainable, for example, from a corresponding acid ester via the corresponding hydrazide and treatment thereof with nitrous acid; azide method), anhydrides with carbonic acid semiderivatives, such as corresponding esters, for example carbonic acid lower alkyl semiesters (obtainable, for example, by treatment of the corresponding acid with haloformic, such as chloroformic, acid lower alkyl esters or with a 1-lower alkoxycarbonyl-2-lower alkoxy-1,2-dihydroquinoline, for example 1-lower alkoxycarbonyl-2-ethoxy-1,2-dihydroquinoline; mixed O-alkylcarbonic acid anhydrides method), or anhydrides with dihalogenated, especially dichlorinated, phosphoric acid (obtainable, for example, by treatment of the corresponding acid with phosphorus oxychloride; phosphorus oxychloride method), or anhydrides with organic acids, such as mixed anhydrides with organic carboxylic acids (obtainable, for example, by treatment of the corresponding acid with an unsubstituted or substituted lower alkane- or phenylalkane-carboxylic acid halide, for example phenylacetic acid chloride, pivalic acid chloride or trifluoroacetic acid chloride; mixed carboxylic acid anhydrides method), with organic sulfonic acids (obtainable, for example, by treatment of a salt, such as an alkali metal salt, of the corresponding acid, with a suitable organic sulfonic acid halide, such as lower alkane- or aryl-, for example methane- or p-toluene-sulfonic acid chloride; mixed sulfonic acid anhydrides method), or with organic phosphonic acids (obtainable, for example, by treatment of the corresponding acid with a suitable organic phosphonic anhydride or phosphonic cyanide; mixed phosphonic acid anhydrides method), and symmetric anhydrides (obtainable, for example, by condensation of the corresponding acid in the presence of a carbodiimide or of 1-diethylaminopropyne; symmetric anhydrides method).

Suitable cyclic amides are especially amides with five-membered diazacycles of aromatic character, such as amides with imidazoles, for example imidazole (obtainable, for example, by treatment of the corresponding acid with N,N'-carbonyldiimidazole; imidazolide method), or pyrazoles, for example 3,5-dimethyl-pyrazole (obtainable, for example, by way of the acid hydrazide by treatment with acetylacetone; pyrazolide method).

Derivatives of the acid of formula 2 wherein the carboxy group is in activated form are preferably formed in situ. For example, N,N'-disubstituted amidino esters can be formed in situ by reacting a mixture of the acid of formula 2 and the amine of formula 3 in the presence of a suitable N,N-disubstituted carbodiimide, for example N,N'-dicyclohexylcarbodiimide. Reactive mixed anhydrides of the acid of formula 2 with an organic phosphonic acid may be formed in situ by reaction with e.g. propylphosphonic anhydride or diethylcyanophosphonate in the presence of suitable base, preferably a tertiary amine, e.g. triethylamine or dimethylaminopyridine.

The reaction can be carried out in a manner known per se, the reaction conditions being dependent especially on whether, and if so how, the carboxy group of the carboxylic acid of formula 2 has been activated, usually in the presence of a suitable solvent or diluent or of a mixture thereof and, if necessary, in the presence of a condensation agent, which, for example when the carboxy group participating in the reaction is in the form of an anhydride, may also be an acid-binding agent, with cooling or heating, for example in a temperature range from approximately −30° C. to approximately +150° C., especially approximately from 0° C. to +100° C., preferably from room temperature (approx. +20° C.) to +70° C., in an open or closed reaction vessel and/or in the atmosphere of an inert gas, for example nitrogen. Customary condensation agents are, for example, carbodiimides, for example N,N'-diethyl-, N,N'-dipropyl-, N,N'-dicyclohexyl- or N-ethyl-N'-(3-dimethylaminopropyl)-carbodiimide, suitable carbonyl compounds, for example carbonyldiimidazole, or 1,2-oxazolium compounds, for example 2-ethyl-5-phenyl-1,2-oxazolium 3'-sulfonate and 2-tert-butyl-5-methyl-isoxazolium perchlorate, or a suitable acylamino compound, for example 2-ethoxy-1-ethoxycarbonyl-1,2-dihydroquinoline. Customary acid-binding condensation agents are, for example, alkali metal carbonates or hydrogen carbonates, for example sodium or potassium carbonate or hydrogen carbonate (customarily together with a sulfate), or organic bases, such as, customarily, pyridine or triethylamine, or sterically hindered tri-lower alkylamines, for example N,N-diisopropyl-N-ethylamine.

In a preferred variant, the carboxylic acid of formula 2 is reacted with an amine of formula 3 in a suitable solvent, such as e.g. N,N-dimethylformamide, in the presence of propylphosphonic anhydride or diethylcyanophosphanate and triethylamine, between 1 and 48 hours at between 0° C. and around 50° C., preferably at room temperature.

If one or more other functional groups, for example carboxy, hydroxy or amino, are or need to be protected in a compound of formula 2 or 3, because they should not take part in the reaction, these are such groups as are usually used in the synthesis of amides, in particular peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference books for peptide synthesis as cited hereinbefore, and in special books on protective groups such as J. F. W. McOmie, "Protective Groups in Organic Chemistry", Plenum Press, London and New York 1973, in "Methoden der organischen Chemie" (Methods of organic chemistry), Houben-Weyl, 4th edition, Volume 15/I, Georg Thieme Verlag, Stuttgart 1974, and in T. W. Greene, "Protective Groups in Organic Synthesis", Wiley, New York.

In the additional process steps, carried out as desired, functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

Salts of a compound of formula 1 with a salt-forming group may be prepared in a manner known per se. Acid addition salts of compounds of formula 1 may thus be obtained by treatment with an acid or with a suitable anion exchange reagent.

Salts can usually be converted to free compounds, e.g. by treating with suitable basic agents, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or In a compound of formula 1 itself. Enantiomers may be separated through the formation of diastereomeric salts, for example by salt formation with an enantiomer-pure chiral acid, or by means of chromatography, for example by HPLC, using chromatographic substrates with chiral ligands.

In a compound of the formula 1 wherein in a group $R_1$ or $R_2$ hydrogen is attached to a nitrogen or oxygen atom and should be converted to the respective compound wherein hydrogen is replaced by lower alkyl, this may be performed by reaction e.g. with a diazo lower alkyl compound, especially diazomethane, in an inert solvent, preferably in the presence of a noble metal catalyst, especially in dispersed form, e.g. copper, or a noble metal salt, e.g. copper(I)-chloride or copper (II)-sulfate. Also reaction with lower alkylhalogenides is possible, or with other leaving group carrying lower alkanes, e.g. lower alkyl alcohols esterified by a strong organic sulfonic acid, such as a lower alkanesulfonic acid (optionally substituted by halogen, such as fluoro), an aromatic sulfonic acid, for example unsubstituted or substituted benzenesulfonic acid, the substituents preferably being selected from lower alkyl, such as methyl, halogen, such as bromo, and/or nitro, e.g. esterified by methanesulfonic acid, or p-toluene sulfonic acid. The alkylation takes place under usual conditions for alkylation of amides, especially in aqueous solution and/or in the presence of polar solvents, typically alcohols, for example methanol, ethanol, isopropanol, or ethylene glycol, or dipolar aprotic solvents, e.g. tetrahydrofuran, dioxane, or dimethylformamide, where applicable in the presence of acidic or basic catalysts, generally at temperatures from about 0° C. to the boiling temperature of the corresponding reaction mixture, preferably between 20° C. and reflux temperature, if necessary under increased pressure, e.g. in a sealed tube, and/or under inert gas, typically nitrogen or argon.

It should be emphasized that reactions analogous to the conversions mentioned in this chapter may also take place at the level of appropriate intermediates.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralising agents, for example ion exchangers, typically cation exchangers, for example in the $H^+$ form, depending on the type of reaction and/or reactants at reduced, normal, or elevated temperature, for example in the range from −100° C. to about 190° C., preferably from about −80° C. to about 150° C., for example at −80 to −60° C., at room temperature, at −20 to 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric mixtures.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described hereinabove as preferred, particularly as especially preferred, primarily preferred, and/or preferred above all.

In the preferred embodiment, a compound of formula 1 is prepared according to or in analogy to the processes and process steps defined in the Examples.

The compounds of formula 1, including their salts, are also obtainable in the form of hydrates, or their crystals can include for example the solvent used for crystallization (present as solvates).

The present invention relates furthermore to a method for the treatment of a neoplastic disease which responds to an inhibition of a protein kinase activity, which comprises administering a compound of formula 1 or a N-oxide or a pharmaceutically acceptable salt thereof, wherein the radicals and symbols have the meanings as defined above for formula 1, in a quantity effective against said disease, to a warm-blooded animal requiring such treatment.

In particular the invention relates to a method for the treatment of leukemia which responds to an inhibition of the Raf and/or Abl tyrosine kinase activity, which comprises administering a compound of formula 1 or a N-oxide or a pharmaceutically acceptable salt thereof, wherein the radicals and symbols have the meanings as defined above for formula 1, in a quantity effective against said leukemia, to a warm-blooded animal requiring such treatment.

The present invention relates also to pharmaceutical compositions that comprise a compound of formula 1 or a N-oxide thereof as active ingredient and that can be used especially in the treatment of the diseases mentioned at the beginning. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention relates especially to pharmaceutical compositions that comprise a compound of formula 1, a tautomer, a N-oxide or a pharmaceutically acceptable salt, or a hydrate or solvate thereof, and at least one pharmaceutically acceptable carrier.

The invention relates also to pharmaceutical compositions for use in a method for the prophylactic or especially therapeutic management of the human or animal body, to a process for the preparation thereof (especially in the form of compositions for the treatment of tumors) and to a method of treating tumor diseases, especially those mentioned hereinabove.

The invention relates also to processes and to the use of compounds of formula 1 or N-oxides thereof for the preparation of pharmaceutical preparations which comprise compounds of formula 1 or N-oxides thereof as active component (active ingredient).

In the preferred embodiment, a pharmaceutical preparation is suitable for administration to a warm-blooded animal, especially humans or commercially useful mammals suffering from a disease responsive to an inhibition of the Abl tyrosine kinase, for example chronic myelogenous leukemia (CML), acute lymphoblastic leukemia (ALL), and the like, and comprises an effective quantity of a compound of formula 1 or N-oxides thereof for the inhibition of a Bcr-Abl fusion protein, also inhibition of a mutated Bcr-Abl fusion protein such as a E255K, E225V, F317L or M351T mutated Bcr-Abl, or a pharmaceutically acceptable salt thereof, if salt-forming groups are present, together with at least one pharmaceutically acceptable carrier. In a preferred embodiment, compounds of formula 1 or N-oxides thereof are useful for the treatment of leukemias resistant to STI571 treatment. Compounds of formula 1 or N-oxides thereof are particularly useful to overcome resistance towards treatment with STI571. Patients with leukemias resistant to STI571 treatment have been described in many publications such as Susan Brandford et al. (Blood. 2002 May 1; 99(9):3472-5), Christophe Barthe et al. or Andreas Hochhaus et al. (Science. 2001 Sep. 21; 293(5538):2163). Preferably, the term "resistant" means that STI571 inhibits the respective functional Abl kinase domain with an $IC_{50}$ that is higher than that of the native human Abl kinase domain, i.e. higher than about 0.025 µM, preferably higher than about 0.15 µM, more preferably higher than about 0.25 µM, most preferably higher than about 5 µM.

In another preferred embodiment, a pharmaceutical preparation is suitable for administration to a warm-blooded animal, especially humans or commercially useful mammals suffering from a disease responsive to an inhibition of the Raf kinase, for example acute myelogenous leukemia or a solid tumor such as colon, lung or pancreatic tumor, and comprises an effective quantity of a compound of formula 1 or N-oxides thereof for the inhibition of the Raf kinase, or a pharmaceutically acceptable salt thereof, if salt-forming groups are present, together with at least one pharmaceutically acceptable carrier.

A pharmaceutical composition for the prophylactic or especially therapeutic management of neoplastic and other proliferative diseases of a warm-blooded animal, especially a human or a commercially useful mammal requiring such treatment, especially suffering from such a disease, comprising as active ingredient in a quantity that is prophylactically or especially therapeutically active against the said diseases a novel compound of formula 1 or N-oxides thereof, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, lipsticks, drops, sprays, dispersions, etc. Examples are capsules containing from about 0.05 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® [polyoxyethylene(20)sorbitan mono-oleate; trademark of ICI Americas, Inc, USA].

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcohol component of these fatty acid esters has a maximum of 6 carbon atoms and is a monovalent or polyvalent, for example a mono-, di- or trivalent, alcohol, for example methanol, ethanol, propanol, butanol or pentanol or the isomers thereof, but especially glycol and glycerol. As fatty acid esters, therefore, the following are mentioned: ethyl oleate, isopropyl myristate, isopropyl palmitate, "Labrafil M 2375" (polyoxyethylene glycerol trioleate from Gattefossé, Paris), "Labrafil M 1944 CS" (unsaturated polyglycolized glycerides prepared by alcoholysis of apricot kernel oil and consisting of glycerides and polyethylene glycol ester; Gattefossé, France), "Labrasol" (saturated polyglycolized glycerides prepared by alcoholysis of TCM and consisting of glycerides and polyethylene glycol ester; Gattefosse, France), and/or "Miglyol 812" (triglyceride of saturated fatty acids of chain length $C_8$ to $C_{12}$ from Hüls AG, Germany), but especially vegetable oils such as cottonseed oil, almond oil, olive oil, castor oil, sesame oil, soybean oil and more especially groundnut oil.

The manufacture of injectable preparations is usually carried out under sterile conditions, as is the filling, for example, into ampoules or vials, and the sealing of the containers.

Pharmaceutical compositions for oral administration can be obtained, for example, by combining the active ingredient with one or more solid carriers, if desired granulating a resulting mixture, and processing the mixture or granules, if desired or necessary, by the inclusion of additional excipients, to form tablets or tablet cores.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

The invention relates likewise to a process or a method for the treatment of one of the pathological conditions mentioned hereinabove, especially a disease which responds to an inhibition of a tyrosine kinase, especially a corresponding neoplastic disease. The compounds of formula 1 or N-oxides thereof can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.05 g to approximately 5 g, preferably from approximately 0.25 g to approximately 1.5 g, of a compound of the present invention.

The present invention relates especially also to the use of a compound of formula 1 or N-oxides thereof, or a pharmaceutically acceptable salt thereof, especially a compound of formula 1 which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, preferably a disease which responds to an inhibition of a protein kinase, especially a neoplastic disease, more especially leukemia which responds to an inhibition of the Abl tyrosine kinase, or a tumor which responds to an inhibition of Raf kinase.

The preferred dose quantity, composition, and preparation of pharmaceutical formulations (medicines) which are to be used in each case are described above.

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the formula 2 and 3 are known, commercially available, or can be synthesized in analogy to or according to methods that are known in the art.

The following Examples serve to illustrate the invention without limiting the invention in its scope.

EXAMPLES

Example 1

4-Diethylamino-N-[4-methyl-3-[[4-(3-pyridinyl)-2-pyrimidinyl]amino]phenyl]-3-(trifluoromethyl)-benzamide A solution containing approximately 50% of propylphosphonic anhydride in N,N-dimethylformamide (Fluka, Buchs, Switzerland; 1.14 mL, ~1.8 mmol) is added to a stirred mixture of 4-methyl-N-[4-(3-pyridinyl)-2-pyrimidinyl]-1,3-benzenediamine (277.3 mg, 1 mmol), 4-diethylamino-3-(trifluoromethyl)-benzoic acid (261.3 mg, 1 mmol) and triethylamine (1.33 mL, 9.6 mmol) in 3 mL N,N-dimethylformamide. After stirring for 24 hours at room temperature, the mixture is treated with a half-saturated aqueous solution of sodium hydrogen carbonate and extracted three times with ethyl acetate. The combined organic extracts are dried ($Na_2SO_4$) and the solvent is evaporated off under reduced pressure. The crude product is purified by column chromatography on silica gel, eluent dichloromethane/methanol. The pure fractions are combined, evaporated and the residue is crystallised from acetone to give the title compound as a white solid.

$^1$H-NMR (400 MHz, DMSO-$d_6$, δ): 0.96 (t, 6H); 2.23 (s, 3H); 3.02 (q, 4H); 7.23 (d, 1H); 7.44 (d, 1H); 7.48 (dd, 1H); 7.51-7.54 (m, 1H); 7.66 (d, 1H); 8.06 (d, 1H); 8.21 (dd, 1H); 8.24 (m, 1H); 8.48 (dt, 1H); 8.52 (d, 1H); 8.68 (dd, 1H); 9.0 (s, 1H); 9.28 (d, 1H); 10.34 (s, 1H).

Example 1.1

4-Diethylamino-3-(trifluoromethyl)-benzonitrile

A mixture of 4-bromo-3-(trifluoromethyl)-benzonitrile (Yonezawa et al., Synthetic Communications (1996), 26, 1575-1578; 6.0 g, 24 mmol), diethylamine (8.3 mL, 80 mmol) and 25 mL N,N-dimethylacetamide is stirred in a tightly closed vessel for 16 hours at 135° C. After cooling, the reaction mixture is treated with a half-saturated aqueous solution of sodium hydrogen carbonate and extracted three times with ethyl acetate. The combined organic extracts are dried ($Na_2SO_4$) and the solvent is evaporated off under reduced pressure. The crude product is purified by column chromatography on silica gel, eluent hexane/ethyl acetate to give the title compound as an orange oil.

$^1$H-NMR (400 MHz, DMSO-$d_6$, δ): 0.96 (t, 6H); 3.08 (q, 4H); 7.61 (d, 1H); 8.04 (dd, 1H); 8.16 (d, 1H).

Example 1.2

4-Diethylamino-3-(trifluoromethyl)-benzoic acid

A mixture of 4-diethylamino-3-(trifluoromethyl)-benzonitrile (1.21 g, 5 mmol), 12 mL of acetic acid and 8 mL of fuming hydrochloric acid (37%) is shaken for 20 hours at 95° C. After cooling, the reaction mixture is evaporated to dryness under reduced pressure. The solid residue is dissolved in a warm half-saturated aqueous sodium carbonate solution and the pH is adjusted to ~5-6 by dropwise addition of 2M hydrochloric acid. The formed precipitate is filtered off, washed with water and dried in vacuo to yield a white solid.

$^1$H-NMR (400 MHz, DMSO-d$_6$, δ): 0.94 (t, 6H); 3.02 (q, 4H); 7.58 (d, 1H); 8.11-8.16 (m, 2H); 13.35 (br., 1H).

Example 2

N-[4-Methyl-3-[[4-(3-pyridinyl)-2-pyrimidinyl]amino]phenyl]-4-(1-pyrrolidinyl)-3-(trifluoromethyl)-benzamide The title compound is prepared using an analogous method as described in Example 1, utilising 4-methyl-N-[4-(3-pyridinyl)-2-pyrimidinyl]-1,3-benzenediamine and 4-(1-pyrrolidinyl)-3-(trifluoromethyl)-benzoic acid as starting materials.

$^1$H-NMR (400 MHz, DMSO-d$_6$, δ): 1.91-1.96 (m, 4H); 2.22 (s, 3H); 3.38-3.46 (m, 4H); 7.06 (d, 1H); 7.20 (d, 1H); 7.43 (d, 1H); 7.48 (dd, 1H); 7.50-7.54 (m, 1H); 8.05-8.07 (m, 2H); 8.24 (d, 1H); 8.48 (dt, 1H); 8.51 (d, 1H); 8.68 (dd, 1H); 8.97 (s, 1H); 9.28 (m, 1H); 10.08 (s, 1H).

Example 2.1

4-(1-Pyrrolidinyl)-3-(trifluoromethyl)-benzonitrile

The title compound is prepared using an analogous method as described in Example 1.1, utilising 4-bromo-3-(trifluoromethyl)-benzonitrile and pyrrolidine (Fluka, Buchs, Switzerland), with a reaction temperature of 95° C.

$^1$H-NMR (400 MHz, DMSO-d$_6$, δ): 1.90-1.96 (m, 4H); 3.39-3.47 (m, 4H); 7.03 (d, 1H); 7.75 (dd, 1H); 7.99 (d, 1H).

Example 2.2

4-(1-Pyrrolidinyl)-3-(trifluoromethyl)-benzoic acid

The title compound is prepared using an analogous method as described in Example 1.2, utilising 4-(1-pyrrolidinyl)-3-(trifluoromethyl)-benzonitrile. The crude product is crystallized from methylene chloride/methanol.

$^1$H-NMR (400 MHz, DMSO-d$_6$, δ): 1.90-1.97 (m, 4H); 3.38-3.45 (m, 4H); 7.01 (d, 1H); 7.90 (dd, 1H); 8.10 (d, 1H); 12.65 (br., 1H).

Example 3

N-[4-Methyl-3-[[4-(3-pyridinyl)-2-pyrimidinyl]amino]phenyl]-4-(4-morpholinyl)-3 (trifluoromethyl)-benzamide The title compound is prepared using an analogous method as described in Example 1, utilising 4-methyl-N-[4-(3-pyridinyl)-2-pyrimidinyl]-1,3-benzenediamine and 4-(4-morpholinyl)-3-(trifluoromethyl)-benzoic acid as starting materials.

$^1$H—NMR (400 MHz, DMSO-d$_6$, δ): 2.23 (s, 3H); 2.96 (m, 4H); 3.74 (m, 4H); 7.23 (d, 1H); 7.44 (d, 1H); 7.48 (dd, 1H); 7.52 (ddd, 1H); 7.66 (d, 1H); 8.07 (d, 1H); 8.23-8.25 (m, 2H); 8.48 (dt, 1H); 8.52 (d, 1H); 8.69 (dd, 1H); 8.99 (s, 1H); 9.28 (m, 1H); 10.34 (s, 1H).

Example 3.1

4-(4-Morpholinyl)-3-(trifluoromethyl)-benzonitrile

The title compound is prepared using an analogous method as described in Example 1.1, utilising 4-bromo-3-(trifluoromethyl)-benzonitrile and morpholine (Fluka, Buchs, Switzerland), with a reaction temperature of 95° C.

$^1$H-NMR (400 MHz, DMSO-d$_6$, δ): 3.00 (m, 4H); 3.72 (m, 4H); 7.60 (d, 1H); 8.09 (dd, 1H); 8.19 (d, 1H).

Example 3.2

4-(4-Morpholinyl)-3-(trifluoromethyl)-benzoic acid

The title compound is prepared using an analogous method as described in Example 1.2, utilising 4-(4-morpholinyl)-3-(trifluoromethyl)-benzonitrile.

$^1$H-NMR (400 MHz, DMSO-d$_6$, δ): 2.92-3.01 (m, 4H); 3.68-3.76 (m, 4H); 7.58 (d, 1H); 8.12-8.19 (m, 2H); 13.25 (br., 1H).

Example 4

N-[4-Methyl-3-[[4-(3-pyridinyl)-2-pyrimidinyl]amino]phenyl]-4-(1-piperidinyl)-3-(trifluoromethyl)-benzamide The title compound is prepared using an analogous method as described in Example 1, utilising 4-methyl-N-[4-(3-pyridinyl)-2-pyrimidinyl]-1,3-benzenediamine and 4-(1-piperidinyl)-3-(trifluoromethyl)-benzoic acid as starting materials.

$^1$H-NMR (400 MHz, DMSO-d$_6$, δ): 1.51-1.70 (m, 6H); 2.23 (s, 3H); 2.89-2.95 (m, 4H); 7.22 (d, 1H); 7.44 (d, 1H); 7.48 (dd, 1H); 7.52 (ddd, 1H); 7.57 (d, 1H); 8.06 (d, 1H); 8.18-8.23 (m, 2H); 8.48 (dt, 1H); 8.51 (d, 1H); 8.68 (dd, 1H); 8.99 (s, 1H); 9.28 (d, 1H); 10.30 (s, 1H).

Example 4.1

4-(1-Piperidinyl)-3-(trifluoromethyl)-benzonitrile

The title compound is prepared using an analogous method as described in Example 1.1, utilising 4-bromo-3-(trifluoromethyl)-benzonitrile and piperidine (Fluka, Buchs, Switzerland), with a reaction temperature of 95° C.

$^1$H-NMR (400 MHz, DMSO-d$_6$, δ): 1.51-1.59 (m, 2H); 1.59-1.68 (m, 4H); 2.93-3.00 (m, 4H); 7.51 (d, 1H); 8.03 (dd, 1H); 8.14 (d, 1H).

Example 4.2

4-(1-Piperidinyl)-3-(trifluoromethyl)-benzoic acid

The title compound is prepared using an analogous method as described in Example 1.2, utilising 4-(1-piperidinyl)-3-(trifluoromethyl)-benzonitrile.

$^1$H-NMR (400 MHz, DMSO-d$_6$, δ): 1.51-1.59 (m, 2H); 1.59-1.69 (m, 4H); 2.89-2.97 (m, 4H); 7.49 (m, 1H); 8.10-8.15 (m, 2H); 13.19 (br., 1H).

Example 5

4-(4-Methyl-1-piperazinyl)-N-[4-methyl-3-[[4-(3-pyridinyl)-2-pyrimidinyl]amino]phenyl]-3-(trifluoromethyl)-benzamide The title compound is prepared using an analogous method as described in Example 1, utilising 4-methyl-N-[4-(3-pyridinyl)-2-pyrimidinyl]-1,3-benzenediamine and 4-(4-methyl-1-piperazinyl)-3-(trifluoromethyl)-benzoic acid as starting materials.

¹H-NMR (400 MHz, DMSO-d₆, δ): 2.23 (s, 3H); 2.39-2.48 (br. s, 3H); 2.63-2.85 (br., 4H); 3.00-3.09 (br.m, 4H); 7.23 (d, 1H); 7.44 (d, 1H); 7.49 (dd, 1H); 7.52 (ddd, 1H); 7.64 (d, 1H); 8.07 (d, 1H); 8.23-8.25 (m, 2H); 8.48 (dt, 1H); 8.52 (d, 1H); 8.69 (dd, 1H); 9.0 (s, 1H); 9.28 (m, 1H); 10.35 (s, 1H)

Example 5.1

4-(4-Methyl-1-piperazinyl)-3-(trifluoromethyl)-benzoic acid

A mixture of 4-bromo-3-(trifluoromethyl)-benzonitrile (Yonezawa et al., Synthetic Communications (1996) 26, 1575-8; 2.47 g, 12 mmol), 1-methylpiperazine (Fluka, Buchs, Switzerland, 5.33 mL, 48 mmol) and 15 mL N,N-dimethylacetamide is stirred in a tightly closed vessel for 14 hours at 95° C. After cooling, the reaction mixture is evaporated to dryness under reduced pressure and the residue is treated with a half-saturated aqueous solution of sodium carbonate and extracted with ethyl acetate. The combined extracts are dried (Na₂SO₄) and the solvent is evaporated off under reduced pressure. The crude product is purified by column chromatography on silica gel, eluent methylene chloride/methanol to give 4-(4-methyl-1-piperazinyl)-3-(trifluoromethyl)-benzonitrile as a pale yellow oil.

A mixture consisting of 30 mL dioxane, 15 mL water and 11.25 mL of 2M aqueous sodium hydroxide solution is added to 4-(4-methyl-1-piperazinyl)-3-(trifluoromethyl)-benzonitrile and the reaction mixture is shaken for 16 hours at 95° C. After cooling, the mixture is evaporated. The resulting residue is treated with water, the pH adjusted to ~5-6 with 1M hydrochloric acid and the solvent evaporated off under reduced pressure. The residue is treated with hot methanol, the insoluble salt filtered off and the filtrate evaporated yielding the crude title compound which is used for the next step without further purification.

¹H-NMR (400 MHz, DMSO-d₆, δ): 2.28 (s, 3H); 2.50-2.58 (m, 4H); 2.94-3.02 (m, 4H); 7.52 (m, 1H); 8.11-8.17 (m, 2H); 13.19 (br., 1H).

Example 6

4-(1H-Imidazol-1-yl)-N-[4-methyl-3-[[4-(3-pyridinyl)-2-pyrimidinyl]amino]phenyl]-3-(trifluoromethyl)-benzamide The title compound is prepared using an analogous method as described in Example 1, utilising 4-methyl-N-[4-(3-pyridinyl)-2-pyrimidinyl]-1,3-benzenediamine and 4-(1H-imidazol-1-yl)-3-(trifluoromethyl)-benzoic acid as starting materials.

¹H-NMR (400 MHz, DMSO-d₆, δ): 2.25 (s, 3H); 7.12-7.15 (m, 1H); 7.26 (d, 1H); 7.43-7.55 (m, 4H); 7.78 (d, 1H); 7.91 (s, 1H); 8.12 (br. 1H); 8.38-8.42 (m, 1H); 8.46-8.54 (m, 3H); 8.67-8.70 (m, 1H); 9.01 (s, 1H); 9.27-9.30 (m, 1H); 10.57 (br.s, 1H).

Example 6.1

4-(1H-Imidazol-1-yl)-3-(trifluoromethyl)-benzonitrile

The title compound is prepared using an analogous method as described in Example 1.1, utilising 4-chloro-3-(trifluoromethyl)-benzonitrile (Lancaster Synthesis, GmbH) and imidazole (Fluka, Buchs, Switzerland), with a reaction temperature of 110° C.

¹H-NMR (400 MHz, DMSO-d₆, δ): 7.13 (m, 1H); 7.47 (s, 1H); 7.85 (d, 1H); 7.91 (s, 1H); 8.37 (dd, 1H); 8.57 (m, 1H).

Example 6.2

4-(1H-Imidazol-1-yl)-3-(trifluoromethyl)-benzoic acid

A mixture of 4-(1H-imidazol-1-yl)-3-(trifluoromethyl)-benzonitrile (1.99 g, 8.4 mmol), 12 mL of acetic acid and 6 mL of 12M hydrochloric acid (37%) is shaken for 16 hours at 95° C. After cooling down the reaction mixture is evaporated under reduced pressure. The resulting residue is dissolved in water and the pH is adjusted to ~5-6 by dropwise addition of 1M sodium hydroxide solution. The precipitate is filtered off, washed with water and dried in vacuo to afford the title compound as a solid.

¹H-NMR (400 MHz, DMSO-d₆, δ): 7.13 (s, 1H); 7.47 (s, 1H); 7.75 (d, 1H); 7.91 (s, 1H); 8.31-8.39 (m, 2H); 13.84 (br., 1H).

Example 7

4-(2-Methyl-1H-imidazol-1-yl)-N-[4-methyl-3-[[4-(3-pyridinyl)-2-pyrimidinyl]amino]phenyl]-3-(trifluoromethyl)-benzamide The title compound is prepared using an analogous method as described in Example 1, utilising 4-methyl-N-[4-(3-pyridinyl)-2-pyrimidinyl]-1,3-benzenediamine and 4-(2-methyl-1H-imidazol-1-yl)-3-(trifluoromethyl)-benzoic acid as starting materials.

¹H-NMR (400 MHz, DMSO-d₆, δ): 2.09 (s, 3H); 2.26 (s, 3H); 6.96 (d, 1H); 7.24-7.28 (m, 2H); 7.45 (d, 1H); 7.50-7.55 (m, 2H); 7.78 (d, 1H); 8.12 (d, 1H); 8.40 (m, 1H); 8.46-8.51 (m, 2H); 8.53 (d, 1H); 8.69 (dd, 1H); 9.03 (s, 1H); 9.30 (d, 1H); 10.59 (s, 1H).

Example 7.1

4-(2-Methyl-1H-imidazol-1-yl)-3-(trifluoromethyl)-benzonitrile

The title compound is prepared using an analogous method as described in Example 1.1, utilising 4-chloro-3-(trifluoromethyl)-benzonitrile (Lancaster Synthesis GmbH) and 2-methyl-imidazole (Fluka, Buchs, Switzerland), with a reaction temperature of 145° C. for 38 hours.

¹H-NMR (400 MHz, DMSO-d₆, δ): 2.06 (s, 3H); 6.95 (m, 1H); 7.25 (m, 1H); 7.86 (d, 1H); 8.39 (dd, 1H); 8.58 (m, 1H).

Example 7.2

4-(2-Methyl-1H-imidazol-1-yl)-3-(trifluoromethyl)-benzoic acid

A mixture of 4-(2-methyl-1H-imidazol-1-yl)-3-(trifluoromethyl)-benzonitrile (1.01 g, 4 mmol), 6 mL of acetic acid and 3 mL of 12M hydrochloric acid (37%) is shaken for 16 hours at 95° C. After cooling, the reaction mixture is evaporated to dryness under reduced pressure. The resulting residue is evaporated twice with toluene, dissolved in water and the pH is adjusted to ~5-6 by dropwise addition of 1M sodium hydroxide solution. The aqueous phase is extracted twice with n-butanol and the organic phase evaporated to yield the title compound as a beige solid.

¹H-NMR (400 MHz, DMSO-d₆, δ): 2.06 (s, 3H); 6.98 (d, 1H); 7.28 (br., 1H); 7.75 (m, 1H); 8.34-8.38 (m, 2H).

Example 8

4-(4-Methyl-1H-imidazol-1-yl)-N-[4-methyl-3-[[4-(3-pyridinyl)-2-pyrimidinyl]amino]phenyl]-3-(trifluoromethyl)-benzamide The title compound is prepared using an analogous method as described in Example 1, utilising 4-methyl-N-[4-(3-pyridinyl)-2-pyrimidinyl]-1,3-benzenediamine and 4-(4-methyl-1H-imidazol-1-yl)-3-(trifluoromethyl)-benzoic acid as starting materials.

¹H-NMR (400 MHz, DMSO-d₆, δ): 2.19 (s, 3H); 2.25 (s, 3H); 7.16 (s, 1H); 7.26 (d, 1H); 7.45 (d, 1H); 7.49-7.56 (m, 2H); 7.72-7.77 (m, 2H); 8.12 (br, 1H); 8.38 (br.d, 1H); 8.45-8.51 (m, 2H); 8.53 (d, 1H); 8.69 (dd, 1H); 9.01 (s, 1H); 9.29 (m, 1H); 10.55 (s, 1H).

Example 8.1

4-(4-Methyl-1H-imidazol-1-yl)-3-(trifluoromethyl)-benzonitrile

The title compound is prepared using an analogous method as described in Example 1.1, utilising 4-chloro-3-(trifluoromethyl)benzonitrile (Lancaster Synthesis GmbH) and 4(5)-methyl-imidazole (Fluka, Buchs, Switzerland), with a reaction temperature of 145° C. for 14 hours.

¹H-NMR (400 MHz, DMSO-d₆, δ): 2.17 (s, 3H); 7.16 (br.s, 1H); 7.76 (br.s, 1H); 7.81 (d, 1H); 8.34 (dd, 1H); 8.53-8.57 (m, 1H).

Example 8.2

4-(4-Methyl-1H-imidazol-1-yl)-3-(trifluoromethyl)-benzoic acid

A mixture of 4-(4-methyl-1H-imidazol-1-yl)-3-(trifluoromethyl)-benzonitrile (1.01 g, 4 mmol), 6 mL of acetic acid and 3 mL of 12 M hydrochloric acid (37%) is shaken for 16 hours at 95° C. After cooling, the reaction mixture is evaporated to dryness under reduced pressure. The resulting residue is evaporated twice with toluene, dissolved in water and the pH is adjusted to ~5-6 by dropwise addition of 1M sodium hydroxide solution. The aqueous phase is extracted twice with ethyl acetate. The organic phase is dried (Na₂SO₄) and evaporated to yield the title compound as a pale yellow solid.

¹H-NMR (400 MHz, DMSO-d₆, δ): 2.18 (s, 3H); 7.16 (br.s, 1H); 7.69-7.77 (m, 2H); 8.30-8.37 (m, 2H).

Example 9

4-(2,4-Dimethyl-1H-imidazol-1-yl)-N-[4-methyl-3-[[4-(3-pyridinyl)-2-pyrimidinyl]amino]phenyl]-3-(trifluoromethyl)-benzamide The title compound is prepared using an analogous method as described in Example 1, utilising 4-methyl-N-[4-(3-pyridinyl)-2-pyrimidinyl]-1,3-benzenediamine and 4-(2,4-dimethyl-1H-imidazol-1-yl)-3-(trifluoromethyl)-benzoic acid as starting materials.

¹H-NMR (400 MHz, DMSO-d₆, δ): 2.03 (s, 3H); 2.11 (s, 3H); 2.25 (s, 3H); 6.94 (s, 1H); 7.26 (d, 1H); 7.45 (d, 1H); 7.49-7.55 (m, 2H); 7.74 (d, 1H); 8.11 (d, 1H); 8.38 (dd, 1H); 8.45 (d, 1H); 8.49 (dt, 1H); 8.53 (d, 1H); 8.69 (dd, 1H); 9.02 (s, 1H); 9.29 (d, 1H); 10.57 (s, 1H).

Example 9.1

4-(2,4-Dimethyl-1H-imidazol-1-yl)-3-(trifluoromethyl)-benzonitrile

The title compound is prepared using an analogous method as described in Example 1.1, utilising 4-chloro-3-(trifluoromethyl)-benzonitrile (Lancaster Synthesis GmbH) and 2,4-dimethyl-imidazole (Trans World Chemicals), with a reaction temperature of 145° C. for 20 hours.

¹H-NMR (400 MHz, DMSO-d₆, δ): 2.01 (s, 3H); 2.09 (s, 3H); 6.93 (s, 1H); 7.81 (d, 1H); 8.36 (dd, 1H); 8.54 (d, 1H).

Example 9.2

4-(2,4-Dimethyl-1H-imidazol-1-yl)-3-(trifluoromethyl)-benzoic acid

A mixture consisting of 11 mL dioxane, 5.5 mL water and 4.9 mL 2M aqueous sodium hydroxide solution is added to 4-(2,4-methyl-1H-imidazol-1-yl)-3-(trifluoromethyl)-benzonitrile (0.65 g, 2.45 mmol) and the reaction mixture shaken for 16 hours at 95° C. After cooling the mixture is evaporated to dryness under reduced pressure. The resulting residue is treated with water, the pH adjusted to ~5-6 with 2M hydrochloric acid and the aqueous phase is extracted twice with n-butanol. The combined organic extracts are evaporated to yield the title compound as a solid.

¹H-NMR (400 MHz, DMSO-d₆, δ): 2.14 (s, 3H); 2.18 (s, 3H); 7.18 (br. s, 1H); 7.81 (d, 1H); 8.31-8.44 (m, 2H).

Example 10

3-(1H-Imidazol-1-yl)-N-[4-methyl-3-[[4-(3-pyridinyl)-2-pyrimidinyl]amino]phenyl]-5-(trifluoromethyl)-benzamide The title compound is prepared using an analogous method as described in Example 1 utilising 4-methyl-N-[4-(3-pyridinyl)-2-pyrimidinyl]-1,3-benzenediamine and 3-(1H-imidazol-1-yl)-5-(trifluoromethyl)-benzoic acid as starting materials.

¹H-NMR (400 MHz, DMSO-d₆, δ): 2.26 (s, 3H); 7.19 (s, 1H); 7.27 (d, 1H); 7.45 (d, 1H); 7.49-7.56 (m, 2H); 8.02 (br, 1H); 8.11 (br.s, 1H); 8.21 (s, 1H); 8.30 (s, 1H); 8.45-8.54 (m, 4H); 8.69 (dd, 1H); 9.01 (s, 1H); 9.30 (m, 1H); 10.50 (br.s, 1H).

Example 10.1

3-(1H-imidazol-1-yl)-5-(trifluoromethyl)-benzonitrile

The title compound is prepared using an analogous method as described in Example 1.1, utilising 3-fluoro-5-(trifluoromethyl)-benzonitrile (Lancaster Synthesis GmbH) and imidazole (Fluka, Buchs, Switzerland), with a reaction temperature of 110° C. for 24 hours.

¹H-NMR (400 MHz, DMSO-d₆, δ): 7.17 (s, 1H); 8.03 (m, 1H); 8.32 (s, 1H); 8.46 (br.s, 1H); 8.54 (d, 1H); 8.62 (m, 1H).

Example 10.2

3-(1H-imidazol-1-yl)-5-(trifluoromethyl)-benzoic acid

The title compound is prepared using an analogous method as described in Example 6.2. utilising 3-(1H-imidazol-1-yl)-5-(trifluoromethyl)-benzonitrile.

¹H-NMR (400 MHz, DMSO-d₆, δ): 7.17 (s, 1H); 8.03 (s, 1H); 8.12 (s, 1H); 8.35 (s, 1H); 8.41 (s, 1H); 8.53 (s, 1H); 13.90 (br., 1H).

Example 11

3-(2-Methyl-1H-imidazol-1-yl)-N-[4-methyl-3-[[4-(3-pyridinyl)-2-pyrimidinyl]amino]phenyl]-5-(trifluoromethyl)-benzamide The title compound is prepared using an analogous method as described in Example 1, utilising 4-methyl-N-[4-(3-pyridinyl)-2-pyrimidinyl]-1,3-benzenediamine and 3-(2-methyl-1H-imidazol-1-yl)-5-(trifluoromethyl)-benzoic acid as starting materials.

¹H-NMR (400 MHz, DMSO-d₆, δ): 2.25 (s, 3H); 2.37 (s, 3H); 6.99 (d, 1H); 7.26 (d, 1H); 7.45 (d, 1H); 7.49-7.54 (m, 3H); 8.10-8.15 (m, 2H); 8.35 (m, 2H); 8.48 (dt, 1H); 8.53 (d, 1H); 8.68 (dd, 1H); 9.01 (s, 1H); 9.29 (m, 1H); 10.49 (s, 1H).

Example 11.1

3-(2-Methyl-1H-imidazol-1-yl)-5-(trifluoromethyl)-benzonitrile

The title compound is prepared using an analogous method as described in Example 1.1, utilising 3-fluoro-5-(trifluoromethyl)-benzonitrile (Lancaster Synthesis GmbH) and 2-methyl-imidazole (Fluka, Buchs, Switzerland), with a reaction temperature of 145° C. for 24 hours.

¹H-NMR (400 MHz, DMSO-d₆, δ): 2.36 (s, 3H); 6.97 (d, 1H); 7.48 (d, 1H); 8.26 (br.s, 1H); 8.41 (m, 1H); 8.46 (br.s, 1H).

Example 11.2

3-(2-Methyl-1H-imidazol-1-yl)-5-(trifluoromethyl)-benzoic acid

The title compound is prepared using an analogous method as described in Example 9.2, utilising 3-(2-methyl-1H-imidazol-1-yl)-5-(trifluoromethyl)-benzonitrile.

¹H-NMR (400 MHz, DMSO-d₆, δ): 2.33 (s, 3H); 6.97 (d, 1H); 7.48 (d, 1H); 8.10 (br., 1H); 8.15 (br., 1H); 8.22 (br., 1H).

Example 12

3-(4-Methyl-1H-imidazol-1-yl)-N-[4-methyl-3-[4-(3-pyridinyl)-2-pyrimidinyl]amino]phenyl-5-(trifluoromethyl)-benzamide The title compound is prepared using an analogous method as described in Example 1, utilising 4-methyl-N-[4-(3-pyridinyl)-2-pyrimidinyl]-1,3-benzenediamine and 3-(4-methyl-1H-imidazol-1-yl)-5-(trifluoromethyl)-benzoic acid as starting materials.

¹H-NMR (400 MHz, DMSO-d₆, δ): 2.20 (s, 3H); 2.26 (s, 3H); 7.27 (d, 1H); 7.45 (d, 1H); 7.49-7.56 (m, 2H); 7.72 (s, 1H); 8.12 (br., 1H); 8.18 (s, 1H); 8.25 (s, 1H); 8.39-8.55 (m, 4H); 8.69 (m, 1H); 9.01 (s, 1H); 9.31 (m, 1H); 10.48 (s, 1H).

Example 12.1

3-(4-Methyl-1H-imidazol-1-yl)-5-(trifluoromethyl)-benzonitrile

The title compound is prepared using an analogous method as described in Example 1.1, utilising 3-fluoro-5-(trifluoromethyl)-benzonitrile (Lancaster Synthesis GmbH) and 4(5)-methyl-imidazole (Fluka, Buchs, Switzerland), with a reaction temperature of 145° C. for 24 hours.

¹H-NMR (400 MHz, DMSO-d₆, δ): 2.18 (s, 3H); 7.74 (m, 1H); 8.27 (br. s, 1H); 8.39 (br.s, 1H); 8.43 (d, 1H); 8.56 (br.s, 1H).

Example 12.2

3-(4-Methyl-1H-imidazol-1-yl)-5-(trifluoromethyl)-benzoic acid

The title compound is prepared using an analogous method as described in Example 9.2, utilising 3-(4-methyl-1H-imidazol-1-yl)-5-(trifluoromethyl)-benzonitrile.

¹H-NMR (400 MHz, DMSO-d₆, δ): 2.27 (s, 3H); 8.00 (s, 1H); 8.18 (s, 1H); 8.40 (m); 8.47 (br., 1H).

Example 13

N-[4-Methyl-3-[[4-(3-pyridinyl)-2-pyrimidinyl]amino]phenyl]-3-(4-morpholinyl)-5-(trifluoromethyl)-benzamide The title compound is prepared using an analogous method as described in Example 1, utilising 4-methyl-N-[4-(3-pyridinyl)-2-pyrimidinyl]-1,3-benzenediamine and 3-(4-morpholinyl)-5-(trifluoromethyl)-benzoic acid as starting materials.

¹H-NMR (400 MHz, DMSO-d₆, δ): 2.24 (s, 3H); 3.28-3.32 (m, 4H); 3.75-3.79 (m, 4H); 7.23 (d, 1H); 7.39 (br., 1H); 7.44 (d, 1H); 7.48 (dd, 1H); 7.51 (ddd, 1H); 7.65 (br., 1H); 7.73 (br., 1H); 8.07 (d, 1H); 8.47 (dt, 1H); 8.52 (d, 1H); 8.68 (dd, 1H); 8.98 (s, 1H); 9.29 (m, 1H); 10.32 (s, 1H).

Example 13.1

3-(4-Morpholinyl)-5-(trifluoromethyl)-benzonitrile

The title compound is prepared using an analogous method as described in Example 1.1, utilising 3-fluoro-5-(trifluoromethyl)-benzonitrile (Lancaster Synthesis GmbH) and morpholine (Fluka, Buchs, Switzerland), with a reaction temperature of 105° C. for 14 hours.

¹H-NMR (400 MHz, DMSO-d₆, δ): 3.25-3.35 (m, 4H); 3.69-3.77 (m, 4H); 7.49 (br.s, 1H); 7.56 (br.s, 1H); 7.66 (br.s, 1H).

Example 13.2

3-(4-Morpholinyl)-5-(trifluoromethyl)-benzoic acid

The title compound is prepared using an analogous method as described in Example 7.2, utilising 3-(4-morpholinyl)-5-(trifluoromethyl)-benzonitrile.

¹H-NMR (400 MHz, DMSO-d₆, δ): 3.20-3.28 (m, 4H); 3.69-3.77 (m, 4H); 7.21 (br.s, 1H); 7.33 (br.s, 1H); 7.43 (br.s, 1H).

Example 14

3-(4-Methyl-1-piperazinyl)-N-[4-methyl-3-[[4-(3-pyridinyl)-2-pyrimidinyl]amino]phenyl]-5-(trifluoromethyl)-benzamide The title compound is prepared using an analogous method as described in Example 1, utilising 4-methyl-N-[4-(3-pyridinyl)-2-pyrimidinyl]-1,3-benzenediamine and 3-(4-methyl-1-piperazinyl)-5-(trifluoromethyl)-benzoic acid as starting materials.

$^1$H-NMR (400 MHz, DMSO-d$_6$, δ): 2.24 (s, 6H); 2.46-2.50 (m, 4H); 3.30-3.36 (m, 4H); 7.24 (d, 1H); 7.37 (br.s, 1H); 7.44 (d, 1H); 7.49 (dd, 1H); 7.52 (dd, 1H); 7.62 (br.s, 1H); 7.72 (br.s, 1H); 8.08 (d, 1H); 8.47 (dt, 1H); 8.52 (d, 1H); 8.70 (dd, 1H); 8.99 (s, 1H); 9.30 (d, 1H); 10.31 (s, 1H).

Example 14.1

3-(4-Methyl-1-piperazinyl)-5-(trifluoromethyl)-benzonitrile

The title compound is prepared using an analogous method as described in Example 1.1, utilising 3-fluoro-5-(trifluoromethyl)-benzonitrile (Lancaster Synthesis GmbH) and 1-methylpiperazine (Fluka, Buchs, Switzerland).

$^1$H-NMR (400 MHz, DMSO-d$_8$, δ): 2.22 (s, 3H); 2.41-2.46 (m, 4H); 3.31-3.37 (m, 4H); 7.48 (br.s, 1H); 7.52 (br.s, 1H); 7.65 (br.s, 1H).

Example 14.2

3-(4-Methyl-1-piperazinyl)-5-(trifluoromethyl)-benzoic acid

A mixture consisting of 50 mL dioxane, 25 mL water and 18.75 mL 2M aqueous sodium hydroxide solution is added to 3-(4-methyl-1-piperazinyl)-5-(trifluoromethyl)-benzonitrile (2.69 g, 10 mmol) and the reaction mixture shaken for 16 hours at 95° C. After cooling, the mixture is evaporated to dryness under reduced pressure. The resulting residue is treated with water, the pH adjusted to ~5-6 with 2M hydrochloric acid. The precipitate is filtered off and the filtrate extracted twice with n-butanol. The combined organic extracts are evaporated to yield the title compound as a solid.

$^1$H-NMR (400 MHz, DMSO-d$_6$, δ): 2.41 (s, 3H); 2.69-2.76 (m, 4H); 3.37-3.42 (m, 4H); 7.45 (br.s, 1H); 7.55 (br.s, 1H); 7.70 (br.s, 1H).

Example 15

4-[[2-(Dimethylamino)ethyl]methylamino]-N-[4-methyl-3-[[4-(3-pyridinyl)-2-Pyrimidinyl]amino]phenyl]-3-(trifluoromethyl)-benzamide The title compound is prepared using an analogous method as described in Example 1, utilising 4-methyl-N-[4-(3-pyridinyl)-2-pyrimidinyl]-1,3-benzenediamine and 4-[[2-(dimethylamino)ethyl]methylamino]-3-(trifluoromethyl)-benzoic acid as starting materials.

$^1$H-NMR (400 MHz, DMSO-d$_6$, δ): 2.10 (s, 6H); 2.23 (s, 3H); 2.35 (m, 2H); 2.78 (s, 3H); 3.14 (m, 2H); 7.22 (d, 1H); 7.43 (d, 1H); 7.48 (dd, 1H); 7.51 (ddd, 1H); 7.59 (d, 1H); 8.07 (d, 1H); 8.16-8.23 (m, 2H); 8.48 (dt, 1H); 8.51 (d, 1H); 8.68 (dd, 1H); 8.99 (s, 1H); 9.28 (m, 1H); 10.28 (s, 1H).

Example 15.1

4-[[2-(Dimethylamino)ethyl]methylamino]-3-(trifluoromethyl)-benzonitrile

The title compound is prepared using an analogous method as described in Example 1.1, utilising 4-chloro-3-(trifluoromethyl)-benzonitrile (Lancaster Synthesis GmbH) and N,N,N'-trimethyl-1,2-ethanediamine (Fluka, Buchs, Switzerland).

$^1$H-NMR (400 MHz, DMSO-d$_6$, δ): 2.09 (s, 6H); 2.38 (t, 2H); 2.86 (s, 3H); 3.24 (t, 2H); 7.45 (d, 1H); 7.94 (dd, 1H); 8.09 (d, 1H).

Example 15.2

4-[[2-(Dimethylamino)ethyl]methylamino]-3-(trifluoromethyl)-benzoic acid

A mixture consisting of 25 mL dioxane, 12.5 mL water and 9.4 mL 2M aqueous sodium hydroxide solution is added to 4-[[2-(dimethylamino)ethyl]methylamino]-3-(trifluoromethyl)-benzonitrile (1.35 g, 5 mmol) and the reaction mixture shaken in for 16 hours at 95° C. After cooling, the mixture is evaporated is evaporated to dryness under reduced pressure. The resulting residue is treated with water, the pH adjusted to ~5 with 1M hydrochloric acid and the mixture evaporated to dryness under reduced pressure. The solid residue is treated with methanol, the suspension filtered and the filtrate evaporated to yield the title compound.

$^1$H-NMR (400 MHz, DMSO-d$_6$, δ): 2.57 (s, 6H); 2.76 (s, 3H); 2.96 (m, 2H); 3.38 (m, 2H); 7.62 (d, 1H); 8.11-8.16 (m, 2H).

Example 16

4-[Methyl-(1-methyl-4-piperidinyl)amino]-N-[4-methyl-3-[[4-(3-Pyridinyl)-2-pyrimidinyl]amino]phenyl]-3-(trifluoromethyl)-benzamide The title compound is prepared using an analogous method as described in Example 1, utilising 4-methyl-N-[4-(3-pyridinyl)-2-pyrimidinyl]-1,3-benzenediamine and 4-[methyl(1-methyl-4-piperidinyl)amino]-5-(trifluoromethyl)-benzoic acid as starting materials.

$^1$H-NMR (400 MHz, DMSO-d$_6$, δ): 1.46-1.57 (m, 2H); 1.62-1.68 (m, 2H); 1.79-1.88 (m, 2H); 2.13 (s, 3H); 2.23 (s, 3H); 2.64 (s, 3H); 2.73-2.80 (m, 2H); 2.87-2.97 (m, 1H); 7.22 (d, 1H); 7.43 (d, 1H); 7.48 (dd, 1H); 7.51 (ddd, 1H); 7.66 (d, 1H); 8.06 (d, 1H); 8.17-8.24 (m, 2H); 8.48 (dt, 1H); 8.51 (d, 1H); 8.68 (dd, 1H); 8.99 (s, 1H); 9.28 (m, 1H); 10.32 (s, 1H)

Example 16.1

4-[Methyl-(1-methyl-4-piperidinyl)amino]-3-(trifluoromethyl)-benzoic acid

The title compound is prepared using an analogous method as described in Example 5.1, utilising 4-chloro-3-(trifluoromethyl)-benzonitrile (Lancaster Synthesis GmbH) and 1-methyl-4-(methylamino)-piperidine (Aldrich, Buchs, Switzerland). Subsequent hydrolysis of the nitrile is carried out with sodium hydroxide in a mixture of dioxane and water as described in Example 5.1.

$^1$H-NMR (400 MHz, DMSO-d$_6$, δ): 1.77-1.86 (m, 4H); 2.54 (s, 3H); 2.63 (s, 3H); 2.65-2.74 (m); 3.13-3.23 (m); 7.63 (d, 1H); 8.12-8.17 (m, 2H).

Example 17

3-Ethylamino-N-[4-methyl-3-[[4-(3-pyridinyl)-2-pyrimidinyl]amino]phenyl]-5-(trifluoromethyl-benzamide The title compound is prepared using an analogous method as described in Example 1, utilising 4-methyl-N-[4-(3-pyridinyl)-2-pyrimidinyl]-1,3-benzenediamine and 3-ethylamino-5-(trifluoromethyl)-benzoic acid as starting materials.

$^1$H-NMR (400 MHz, DMSO-d$_6$, δ): 1.19 (t, 3H); 2.23 (s, 3H); 3.14 (m, 2H); 6.36 (t, 1H); 6.98 (br. s, 1H); 7.22 (d, 1H); 7.32 (br. s, 1H); 7.37 (br. s, 1H); 7.43 (d, 1H); 7.48 (dd, 1H); 7.51 (dd, 1H); 8.06 (d, 1H); 8.48 (dt, 1H); 8.51 (d, 1H); 8.68 (dd, 1H); 9.00 (s, 1H); 9.28 (m, 1H); 10.25 (s, 1H).

Example 17.1

3-Ethylamino-5-(trifluoromethyl)-benzoic acid methyl ester

A mixture of 3-amino-5-(trifluoromethyl)-benzoic acid methyl ester (J. Med. Chem. (1969) 12, 299-303; 4.23 g, 19.3 mmol), potassium carbonate (8.0 g, 57.9 mmol) and iodoethane (3.12 mL, 38.6 mmol) in 20 mL N,N-dimethylformamide is stirred at 65° C. for 14 hours in a tightly closed vessel. After cooling, the reaction mixture is filtered and the filtrate evaporated to dryness under reduced pressure. The residue is treated with water and extracted three times with ethyl acetate. The combined extracts are dried (Na$_2$SO$_4$) and the solvent is evaporated off under reduced pressure. The resulting residue is purified by column chromatography on silica gel, eluent hexane/methylene chloride (1:1).

$^1$H-NMR (400 MHz, DMSO-d$_6$, δ): 1.18 (t, 3H); 3.10 (m, 2H); 3.85 (s, 3H); 6.46 (t, 1H); 7.02 (br. 1H); 7.29 (br.s, 1H); 7.37 (br., 1H).

Example 17.2

3-Ethylamino-5-(trifluoromethyl)-benzoic acid

A mixture of 3-ethylamino-5-(trifluoromethyl)-benzoic acid methyl ester (1.38 g, 5.6 mmol), 5.5 mL 1M aqueous sodium hydroxide solution in 12 mL ethanol is shaken for 4 hours at 70° C. After cooling, the mixture is evaporated to dryness under reduced pressure. The resulting residue is dissolved in water, the pH adjusted to 5 with 1M hydrochloric acid. The precipitate is filtered off, washed with water and dried in vacuo to give the title compound.

$^1$H-NMR (400 MHz, DMSO-d$_6$, δ): 1.18 (t, 3H); 3.10 (m, 2H); 6.39 (m, 1H); 6.99 (br.s, 1H); 7.29 (br.s, 1H); 7.36 (br.s, 1H); 13.15 (br., 1H).

Example 18

3-Acetylamino-N-[4-methyl-3-[[4-(3-pyridinyl)-2-pyrimidinyl]amino]phenyl]-5-(trifluoromethyl)-benzamide Diethylcyanophosphonate (Aldrich, Buchs, Switzerland; 0.66 mL, 4.0 mmol) is added to a stirred mixture of 4-methyl-N-[4-(3-pyridinyl)-2-pyrimidinyl]-1,3-benzenediamine (554 mg, 2.0 mmol), 3-acetylamino-5-(trifluoromethyl)-benzoic acid (495 mg, 2.0 mmol) and triethylamine (1.12 mL, 8.0 mmol) in 10 mL N,N-dimethylformamide at 20° C. under an argon atmosphere. After stirring for 18 hours at 20° C., the mixture is treated with saturated aqueous solution of sodium hydrogen carbonate and extracted twice with ethyl acetate. The combined extracts are dried (MgSO$_4$), filtered and the solvent is evaporated off under reduced pressure to afford a crude product. The crude product is purified by column chromatography on silica gel, eluent dichloromethane/methanol/aqueous ammonia. The pure fractions are combined, the solvent is evaporated off under reduced pressure and the residue is crystallised from ethyl acetate-hexane to give the title compound as a cream crystalline solid.

$^1$H-NMR (400 MHz, DMSO-d$_6$, δ): 2.10 (s, 3H); 2.23 (s, 3H); 7.22 (dd, 1H); 7.43 (dd, 1H); 7.45-7.50 (m, 1H); 7.51-7.54 (m, 1H); 7.97 (d, 1H); 8.04 (d, 1H); 8.24 (dd, 1H); 8.28 (m, 1H); 8.49 (dt, 1H); 8.50 (dd, 1H); 8.68 (dd, 1H); 8.99 (s, 1H); 9.25 (d, 1H); 10.43 (dd, 1H).

Example 18.1

3-Acetylamino-5-(trifluoromethyl)-benzoic acid

A mixture of 3-nitroo-5-(trifluoromethyl)benzoic acid (5.10 g, 20 mmol) and acetic anhydride (2.1 mL, 22 mmol) in 50 mL pyridine is stirred at 22° C. for 14 hours. The mixture is then evaporated to dryness under reduced pressure to give a residue which is treated with 2M hydrochloric acid and extracted three times with ethyl acetate. The combined extracts are washed with water, dried (MgSO$_4$) and the solvent is evaporated off under reduced pressure to yield the crude product which is purified by recrystallisation from ethyl acetate-hexane to give the title compound as a beige crystalline solid, m.p. 194-220° C.

$^1$H-NMR (400 MHz, DMSO-d$_6$, δ): 7.80 (d, 1H); 8.27 (d, 1H); 8.35 (d, 1H); 10.46 (s, 1H); 13.50 (br.s, 1H).

Example 18.2

3-Amino-5-(trifluoromethyl)-benzoic acid

A solution of 3-nitro-5-(trifluoromethyl)benzoic acid (Lancaster Synthesis GmbH; 11.75 g, 50 mmol) in ethanol (300 mL) is hydrogenated at atmospheric pressure over Raney nickel (1 g) at 40° C. The calculated amount of hydrogen is taken up after 8 hours. The mixture is then filtered and the solvent is evaporated off under reduced pressure to yield the crude product which is purified by recrystallisation from diethylether-hexane to give the title compound as a beige crystalline solid, m.p. 134-139° C.

$^1$H-NMR (400 MHz, DMSO-d$_6$, δ): 5.86 (br.s, 2H); 7.02 (d, 1H); 7.24 (d, 1H); 7.38 (d, 1H); 13.11 (br.s, 1H).

Example 19

Soft Capsules 5000 soft gelatin capsules, each comprising as active ingredient 0.05 g of one of the compounds of formula 1 mentioned in the preceding Examples, are prepared as follows: 250 g pulverized active ingredient is suspended in 2 L Lauroglykol® (propylene glycol laurate, Gattefossé S. A., Saint Priest, France) and ground in a wet pulverizer to produce a particle size of about 1 to 3 μm. 0.419 g portions of the mixture are then introduced into soft gelatin capsules using a capsule-filling machine.

Example 20

Pharmacokinetic Data

The compound of formula 1 to be tested is formulated for administration to female OF1 mice from IFACREDO, France, by first dissolving in N-methyl-pyrrolidone (NMP), and then by diluting with PEG300 to a final concentration of 10% v/v NMP: 90% v/v PEG300, producing a clear solution of the compound. The concentrations were adjusted to deliver a constant volume of 10 mL/kg body weight. The compound is prepared immediately before use. The formulated compound is administered perorally by gavage to provide dosages of 50 mg/kg. At the allotted time points mice (4 at each time) are anesthetized with 3% isoflurane in medical oxygen and blood samples are obtained by heart puncture into heparinized tubes (ca. 30 IU/mL). The animals are subsequently killed without recovering from the anesthetic. Plasma is prepared from the blood by centrifugation (10,000 g, 5 min) and either analyzed immediately or stored frozen at −70° C.

The plasma samples (10-250 μL) are e.g. spiked with 5 μL of internal standard, mixed with 200 μL 0.1 M NaOH and 500 μL Chloroform in a 1.5 mL Eppendorf tube and shaken vigorously for 10 minutes on an Eppendorf mixer. Thereafter, the mixture is centrifuged (3 min at 10,000×g), the organic phase transferred to a second Eppendorf tube and evaporated to dryness in a vacuum centrifuge (Speedvac 5301). The dry residue e.g. is dissolved in 250 μL of 10% v/v Acetonitrile in water containing 0.1% formic acid. The subsequent analysis is carried out e.g. by high-pressure liquid chromatography/tandem mass spectrometry (HPLC/MS-MS) using an Agilent 1100 Series (Agilent, Palo Alto, Calif., USA) HPLC system with vacuum degasser, binary pump, and thermostated column compartment combined with a cooled autosampler system (HTS PAL, CTC Analytics, Zwingen, Switzerland). The sample (5-15 μL) is injected e.g. onto an Ultra Phenyl column (particle size 3 μm, 50×1 mm; Restek, Bellefonte, USA) with a guard column (4×2 mm) of the same material (Phenomenex, Torrance, USA). After equilibration e.g. with water and a latency period of 1 min the sample is eluted e.g. by a linear gradient of 0-100% acetonitrile in water containing 0.2% v/v formic acid over a period of 11 min at a flow rate of 60 μL/min. The column is prepared for the next sample e.g. by re-equilibrating for 3 min with 100% water to the starting conditions. The separation is performed e.g. at a column temperature of 40° C. The column effluent is introduced e.g. directly into the ion source of a triple stage quadropole mass spectrometer (Quattro Ultima™, Micromass, Manchester, UK) controlled by Masslynx™ 3.5 software (Micromass, Manchester, UK) using as ionization technique electrospray ionization positive mode (ESI+). The compound is detected by MS/MS following fragmentation of the parent ions. The limit of quantitation is determined at e.g. 0.002 nmol/L. A calibration curve is constructed with known amounts of compound including a fixed amount of internal standard in plasma which is processed as described above. The concentration of unknown samples is calculated from a plot of the peak area ratio of the selected daughter ion of the analyte to the product of its internal standard (ordinate) against the nominal concentration (abscissa). Regression analysis is performed using Quanlynx™, Masslynx™ software 3.5 (Micromass, Manchester, UK).

Example 21

In Vitro Inhibition Data

Enzymatic (c-Abl, Bcr-Abl) in vitro inhibition data are shown in the accompanying table. Values of $IC_{50}$ (in nM) are expressed as a range, within which individual $IC_{50}$ measurements fall. Corresponding mean values (±SEM) for the compound known as STI571 are 170±23 nM (c-Abl, $IC_{50}$; 23 determinations) and 198±7 nM (Bcr-Abl, $IC_{50}$; 71 determinations).

| Example | c-Abl, $IC_{50}$ (nM) | Bcr-Abl, $IC_{50}$ (nM) |
| --- | --- | --- |
| 1 | 50-100 | 200-500 |
| 2 | 10-60 | 100-300 |
| 3 | 40-100 | 20-100 |
| 4 | 60-110 | 80-200 |
| 5 | 5-50 | 30-100 |
| 6 | 5-20 | 10-50 |
| 7 | 5-20 | 10-50 |
| 8 | 5-20 | 10-50 |
| 9 | 5-20 | 20-80 |
| 10 | 5-20 | 10-50 |
| 11 | 5-20 | 10-50 |
| 12 | 5-20 | 10-50 |
| 13 | 5-20 | 20-80 |
| 14 | 5-20 | 30-180 |
| 15 | 5-20 | 50-200 |
| 16 | 5-20 | 50-200 |
| 17 | 10-70 | 20-60 |
| 18 | | 13 |

What is claimed is:
1. A compound of formula 1

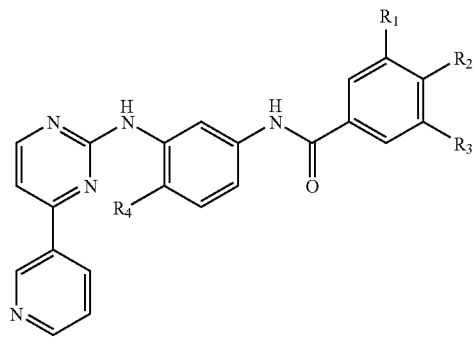

wherein
$R_1$ represents hydrogen and $R_2$ represents $NR_5R_6$, or $R_1$ represents $NR_5R_6$ and $R_2$ represents hydrogen;
$R_3$ represents lower alkyl, fluoroalkyl, hydroxyalkyl or carbamoyl;
$R_4$ represents hydrogen, lower alkyl or halogen; and
$R_5$ and $R_6$ represent, independently of each other, hydrogen, lower alkyl, hydroxy-lower alkyl, lower alkoxy-lower alkyl, lower acyloxy-lower alkyl, carboxy-lower alkyl, lower alkoxycarbonyl-lower alkyl, amino-lower alkyl, lower alkylamino-lower alkyl, di(lower alkyl)amino-lower alkyl, N-lower alkylpiperidinyl, N-lower alkylpyrrolidinyl, or lower acyl, or $R_5R_6$ together represent alkylene with four, five or six carbon atoms, oxa-lower alkylene with one oxygen and three or four carbon atoms, or aza-lower alkylene with one nitrogen and three or four carbon atoms wherein the nitrogen atom is unsubstituted or substituted by lower alkyl, hydroxy-lower alkyl or lower alkoxy-lower alkyl, and wherein lower alkylene in each case may be partially or totally unsaturated and/or the carbon atoms of lower alkylene may be substituted by lower alkyl, hydroxy or lower alkoxy;
and a N-oxide or a pharmaceutically acceptable salt of such a compound.
2. A compound of formula 1 according to claim 1 wherein $R_1$ represents hydrogen and $R_2$ represents $NR_5R_6$, or $R_1$ represents $NR_5R_6$ and $R_2$ represents hydrogen;

$R_3$ represents lower alkyl, fluoroalkyl, hydroxyalkyl or carbamoyl;

$R_4$ represents lower alkyl; and $R_5$ and $R_6$ represent, independently of each other, hydrogen, lower alkyl, hydroxy-lower alkyl, lower alkoxy-lower alkyl, lower acyloxy-lower alkyl, carboxy-lower alkyl, lower alkoxycarbonyl-lower alkyl, amino-lower alkyl, lower alkylamino-lower alkyl, di(lower alkyl)amino-lower alkyl, N-lower alkylpiperidinyl, N-lower alkylpyrrolidinyl, or lower acyl, or $R_5R_6$ together represent alkylene with four, five or six carbon atoms, oxa-lower alkylene with one oxygen and three or four carbon atoms, or aza-lower alkylene with one nitrogen and three or four carbon atoms wherein the nitrogen atom is unsubstituted or substituted by lower alkyl, hydroxy-lower alkyl or lower alkoxy-lower alkyl, and wherein lower alkylene in each case may be partially or totally unsaturated and/or the carbon atoms of lower alkylene may be substituted by lower alkyl, hydroxy or lower alkoxy;

and a N-oxide or a pharmaceutically acceptable salt of such a compound.

3. A compound of formula 1 according to claim 1 wherein $R_1$ represents hydrogen and $R_2$ represents $NR_5R_6$, or $R_1$ represents $NR_5R_6$ and $R_2$ represents hydrogen;

$R_3$ represents trifluoromethyl;

$R_4$ represents methyl; and $R_5$ and $R_6$ represent, independently of each other, hydrogen, lower alkyl, hydroxy-lower alkyl, lower alkoxy-lower alkyl, lower acyloxy-lower alkyl, carboxy-lower alkyl, lower alkoxycarbonyl-lower alkyl, amino-lower alkyl, lower alkylamino-lower alkyl, di(lower alkyl)amino-lower alkyl, N-lower alkylpiperidinyl, N-lower alkylpyrrolidinyl, or acetyl, or $R_5R_6$ together represent alkylene with four, five or six carbon atoms, oxa-lower alkylene with one oxygen and three or four carbon atoms, or aza-lower alkylene with one nitrogen and three or four carbon atoms wherein the nitrogen atom is unsubstituted or substituted by lower alkyl, hydroxy-lower alkyl or lower alkoxy-lower alkyl, and wherein lower alkylene in each case may be partially or totally unsaturated and/or the carbon atoms of lower alkylene may be substituted by lower alkyl, hydroxy or lower alkoxy;

and a N-oxide or a pharmaceutically acceptable salt of such a compound.

4. A compound of formula 1 according to claim 1 wherein $R_1$ represents hydrogen and $R_2$ represents $NR_5R_6$, or $R_1$ represents $NR_5R_6$ and $R_2$ represents hydrogen;

$R_3$ represents trifluoromethyl;

$R_4$ represents methyl; and $R_5$ and $R_6$ represent, independently of each other, hydrogen, lower alkyl, hydroxy-lower alkyl, amino-lower alkyl, lower alkylamino-lower alkyl, di(lower alkyl)amino-lower alkyl, N-lower alkylpiperidinyl, or lower acyl, or $R_5R_6$ together represent alkylene with four or five carbon atoms, oxa-lower alkylene with one oxygen and three or four carbon atoms, or aza-lower alkylene with one nitrogen and three or four carbon atoms wherein the nitrogen atom is unsubstituted or substituted by lower alkyl, hydroxy-lower alkyl or lower alkoxy-lower alkyl, and wherein lower alkylene in each case may be partially or totally unsaturated and/or the carbon atoms of lower alkylene may be substituted by lower alkyl;

and a N-oxide or a pharmaceutically acceptable salt of such a compound.

5. A compound of formula 1 according to claim 1 wherein $R_1$ represents hydrogen and $R_2$ represents $NR_5R_6$, or $R_1$ represents $NR_5R_6$ and $R_2$ represents hydrogen;

$R_3$ represents trifluoromethyl;

$R_4$ represents methyl; and $R_5$ and $R_6$ represent, independently of each other, hydrogen, lower alkyl, di(lower alkyl)amino-lower alkyl, N-lower alkylpiperidinyl, or lower acetyl, or $R_5R_6$ together represent alkylene with four or five carbon atoms, oxa-lower alkylene with one oxygen and four carbon atoms, or aza-lower alkylene with one nitrogen and three or four carbon atoms wherein the nitrogen atom is unsubstituted or substituted by lower alkyl, and wherein aza-lower alkylene may be unsaturated and/or the carbon atoms of aza-lower alkylene may be substituted by lower alkyl;

and a N-oxide or a pharmaceutically acceptable salt of such a compound.

6. A compound of formula 1 according to claim 1 wherein $R_1$ represents hydrogen and $R_2$ represents $NR_5R_6$, or $R_1$ represents $NR_5R_6$ and $R_2$ represents hydrogen;

$R_3$ represents trifluoromethyl;

$R_4$ represents methyl; and $R_5$ and $R_6$ represent, independently of each other, hydrogen, methyl, ethyl, 2-dimethylaminoethyl, 4-methyl-1-piperidinyl, or acetyl, or $NR_5R_6$ together represent pyrrolidino, piperidino, morpholino, N-methylpiperazino, 1H-imidazolyl, 1H-2-methylimidazolyl, 1H-4-methylimidazolyl or 1H-2,4-dimethylimidazolyl;

and a N-oxide or a pharmaceutically acceptable salt of such a compound.

7. A process for the synthesis of a compound of the formula 1

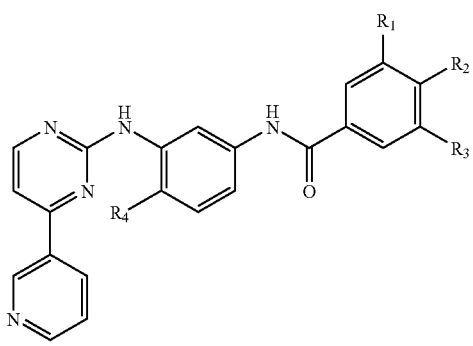

or an N-oxide or a salt thereof, wherein the symbols $R_1$, $R_2$, $R_3$ and $R_4$ are as defined in claim 1, characterized in that a compound of formula 2

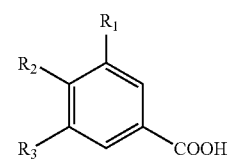

wherein $R_1$, $R_2$ and $R_3$ are as defined for a compound of formula 1, or a derivative thereof wherein the carboxy group —COOH is in activated form, is reacted with an amine of the formula 3

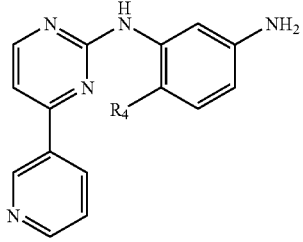

wherein $R_4$ is as defined for a compound of the formula 1, optionally in the presence of a dehydrating agent and an inert base and/or a suitable catalyst, and optionally in the presence of an inert solvent;

where the above starting compounds of formula 2 and 3 may also be present with functional groups in protected form if necessary and/or in the form of salts, provided a salt-forming group is present and the reaction in salt form is possible;

any protecting groups in a protected derivative of a compound of the formula 1 are removed;

and, if so desired, an obtainable compound of formula 1 is converted into another compound of formula 1 or a N-oxide thereof, a free compound of formula 1 is converted into a salt, an obtainable salt of a compound of formula 1 is converted into the free compound or another salt, and/or a mixture of isomeric compounds of formula 1 is separated into the individual isomers.

8. A pharmaceutical composition comprising as an active ingredient a compound of formula 1 according to claim 1 or a N-oxide or a pharmaceutically acceptable salt thereof together with a pharmaceutically acceptable carrier.

9. A method for the treatment of a disease which responds to an inhibition of protein kinase activity, which comprises administering a compound of formula 1 according to claim 1 or a N-oxide or a pharmaceutically acceptable salt thereof, wherein said disease is a leukemia which responds to an inhibition of the Raf and/or Abl tyrosine kinase activity.

\* \* \* \* \*